(12) United States Patent
Chen et al.

(10) Patent No.: US 10,724,069 B2
(45) Date of Patent: Jul. 28, 2020

(54) METHODS AND DEVICES FOR CELL DETECTION

(71) Applicant: ChipCare Corporation, Toronto (CA)

(72) Inventors: Lu Chen, Thornhill (CA); James Jiahua Dou, Oakville (CA); James Andrew Fraser, Toronto (CA); Rakesh Kumar Nayyar, Thornhill (CA)

(73) Assignee: CHIPCARE CORPORATION, Toronto, ON (CA)

( * ) Notice: Subject to any disclaimer, the term of this patent is extended or adjusted under 35 U.S.C. 154(b) by 0 days.

(21) Appl. No.: 15/515,517

(22) PCT Filed: Sep. 29, 2015

(86) PCT No.: PCT/IB2015/002084
§ 371 (c)(1),
(2) Date: Mar. 29, 2017

(87) PCT Pub. No.: WO2016/051272
PCT Pub. Date: Apr. 7, 2016

(65) Prior Publication Data
US 2017/0218425 A1    Aug. 3, 2017

Related U.S. Application Data

(60) Provisional application No. 62/056,718, filed on Sep. 29, 2014.

(51) Int. Cl.
| *C12Q 1/06* | (2006.01) |
| *A61B 5/151* | (2006.01) |
| *A61B 5/15* | (2006.01) |
| *A61B 5/157* | (2006.01) |
| *G01N 15/14* | (2006.01) |
| *G01N 15/10* | (2006.01) |
| *G01N 15/00* | (2006.01) |
| *B01L 9/00* | (2006.01) |
| *B01L 3/00* | (2006.01) |
| *G06K 9/00* | (2006.01) |
| *G06T 7/00* | (2017.01) |

(52) U.S. Cl.
CPC ............... *C12Q 1/06* (2013.01); *A61B 5/151* (2013.01); *A61B 5/157* (2013.01); *A61B 5/150022* (2013.01); *A61B 5/150305* (2013.01); *A61B 5/150343* (2013.01); *A61B 5/150358* (2013.01); *A61B 5/150412* (2013.01); *A61B 5/150503* (2013.01); *A61B 5/150755* (2013.01); *A61B 5/150763* (2013.01); *A61B 5/150824* (2013.01); *A61B 5/150854* (2013.01); *B01L 3/502715* (2013.01); *B01L 3/502761* (2013.01); *B01L 9/527* (2013.01); *G01N 15/1459* (2013.01); *G01N 15/1484* (2013.01); *G06K 9/00134* (2013.01); *G06T 7/0012* (2013.01); *B01L 2200/04* (2013.01); *B01L 2200/0647* (2013.01); *B01L 2200/16* (2013.01); *B01L 2300/024* (2013.01); *B01L 2300/0654* (2013.01); *B01L 2300/0816* (2013.01); *B01L 2300/0877* (2013.01); *B01L 2300/0887* (2013.01); *B01L 2400/0481* (2013.01); *B01L 2400/0487* (2013.01); *G01N 2015/0065* (2013.01); *G01N 2015/1006* (2013.01); *G06T 2207/30024* (2013.01)

(58) Field of Classification Search
None
See application file for complete search history.

(56) References Cited

U.S. PATENT DOCUMENTS

| 6,382,254 B1 * | 5/2002 | Yang ................ A61M 5/16881 137/341 |
| 8,609,336 B2 | 12/2013 | Dahlberg et al. |
| 2001/0041333 A1 | 11/2001 | Short et al. |
| 2002/0051971 A1 | 5/2002 | Stuelpnagel et al. |
| 2004/0132122 A1 | 7/2004 | Banerjee et al. |
| 2006/0134774 A1 | 6/2006 | Clausen et al. |
| 2007/0086918 A1 | 4/2007 | Hartley et al. |

(Continued)

FOREIGN PATENT DOCUMENTS

| DE | 102008021364 A1 | 6/2009 |
| EP | 0733714 A2 | 9/1996 |

(Continued)

OTHER PUBLICATIONS

Yager, P. et al. 2006. Microfluidic diagnostic technologies for global public health. Nature 442: 412-418. specif. pp. 412, 413, 415, 417.*
Sheybani, R. et al. Feb. 2013. A MEMS electrochemical bellows actuator for fluid metering applications. Biomedical Microdevices 15(1): 37-48; pp. 1-28. specif. pp. 1, 2, 4.*
Song, H. et al. 2006. Reactions in droplets in microfluidic channels. Angewandte Chemie International Edition 45: 7336-7356. specif. pp. 7337, 7340, 7342, 7343, 7345, 7346.*
Poole, R.J. et al. Jul. 15, 2013. Viscoelastic seconary flows in serpentine channels. Journal of non-Newtonian fluid mechanics 201: 10-16. specif. pp. 10, 12.*

(Continued)

*Primary Examiner* — Thomas J. Visone
*Assistant Examiner* — Sharon M. Papciak
(74) *Attorney, Agent, or Firm* — Wilson Sonsini Goodrich & Rosati

(57) ABSTRACT

The present disclosure relates to a cartridge, detection module, system, and kit for cell and particle detection and analysis. Devices disclosed herein may include at least an optical source, a fluidic chip, and a detection module, wherein the sample flows within the fluidic chip past a detection window, where the cells or particles are imaged by an image acquisition and analysis module that may include an optical detector. The image acquisition and analysis module may count the cells or particles of interest in real-time, or near real-time, or the module may capture images of the cells in order to analyze the sample from combined images at a later time.

11 Claims, 16 Drawing Sheets

(56) References Cited

U.S. PATENT DOCUMENTS

| | | | |
|---|---|---|---|
| 2008/0176242 A1 | 7/2008 | McMaster et al. | |
| 2009/0042737 A1 | 2/2009 | Katz et al. | |
| 2009/0081773 A1 | 3/2009 | Kaufman | |
| 2010/0267049 A1* | 10/2010 | Rutter | G01N 21/6428 435/7.1 |
| 2010/0291584 A1 | 11/2010 | Tseng et al. | |
| 2011/0022331 A1* | 1/2011 | Clinton | B01L 3/54 702/27 |
| 2012/0177543 A1* | 7/2012 | Battrell | B01F 11/0071 422/187 |
| 2014/0170679 A1 | 6/2014 | Aitchison et al. | |
| 2014/0274778 A1 | 9/2014 | Tsao et al. | |
| 2017/0343466 A1 | 11/2017 | Dou | |

FOREIGN PATENT DOCUMENTS

| | | |
|---|---|---|
| EP | 1418233 A1 | 5/2004 |
| EP | 2437890 A1 | 4/2012 |
| EP | 3201311 A1 | 8/2017 |
| EP | 3224594 A1 | 10/2017 |
| WO | WO-2005066368 A2 | 7/2005 |
| WO | WO-2005106024 A1 | 11/2005 |
| WO | WO-2007133710 A2 | 11/2007 |
| WO | WO-2009063379 A1 | 5/2009 |
| WO | WO-2010115167 A2 | 10/2010 |
| WO | WO-2010139295 | 12/2010 |
| WO | WO-2012119243 A2 | 9/2012 |
| WO | WO-2012154306 A1 | 11/2012 |
| WO | WO-2015001070 A1 | 1/2015 |
| WO | WO-2016051272 A1 | 4/2016 |
| WO | WO-2016083898 A1 | 6/2016 |

OTHER PUBLICATIONS

Anonymous, BD Cytometric Bead Array: Multiplexed Bead-Based Immunoassays. pp. 1-14, 2012. [retrieved on Mar. 31, 2016]. Retrieved from the Internet< URL: https://www.bdbiosciences.com/documents/CBA_Brochure_Intl.pdf>.

PCT/EP2014/064290 International Preliminary Report on Patentability dated Jan. 5, 2016.

PCT/EP2014/064290 International Search Report and Written Opinion dated Sep. 29, 2014.

PCT/IB2015/002084 International Preliminary Report on Patentability dated Apr. 13, 2017.

PCT/IB2015/002460 International Search Report and Written Opinion dated Sep. 29, 2014.

Vostry, Multiplex immunoassays: Chips and beads. Journal of the International Federation of Clinical Chemistry and Laboratory Medicine. 20(4):4 pages, 2009.

Kuo et al., Deformability considerations in filtration of biological cells. Lab On a Chip, 10(7):837-842, 2010.

Li, Paul C.H. et al., Imaging for degradation of ikB-EGFP in a single Jurkat T cell studied within a microfluidic channel. 7th International Conference on Miniaturized Chemical and Biochemical Analysis Systems, Squaw Valley, CA, p. 1149-1152, Oct. 5-9, 2003.

PCT Patent Application No. PCT/CA2012/000227 International Preliminary Report on Patentability dated Jul. 17, 2013.

PCT Patent Application No. PCT/CA2012/000227 International Search Report and Written Opinion dated Oct. 17, 2012.

PCT Patent Application No. PCT/IB2015/002084 International Search Report and Written Opinion dated Feb. 22, 2016.

Taylor et al., Dynamic analysis of MARK signaling using a high-throughput microfluidic single-cell imaging platform. PNAS, 105(10):3758-3763, 2009.

Zhao et al., Method for the accurate preparation of cell-spiking standards. Anal. Chem., 81(3):1285-1290, 2009.

Braeckmans, et al. Encoding Microcarriers: Present and Future Technologies. Nature Reviews Drug Discovery. 2002; 1:447-456.

Dunbar et al. Introduction to Luminex? xMAP? Technology and Applications for Biological Analysis in China. Asiobiotec 14(10):26-30 (2010).

European Patent Application No. 15847832.1 Extended Search Report dated May 24, 2018.

European Patent Application No. 15862356.1 Extended Search Report dated Jul. 5, 2018.

Nguyen et al. MEMS-Micropumps: A Review. J Fluids Eng 124(2):384-392 (2002).

PCT/IB2015/002460 International Preliminary Report on Patentability dated May 30, 2017.

U.S. Appl. No. 15/531,397 Restriction Requirement dated Sep. 4, 2018.

Chinese Patent Application No. 201580074823.1 First Office Action dated May 22, 2019.

U.S. Appl. No. 15/531,397 Office Action dated Mar. 19, 2019.

* cited by examiner

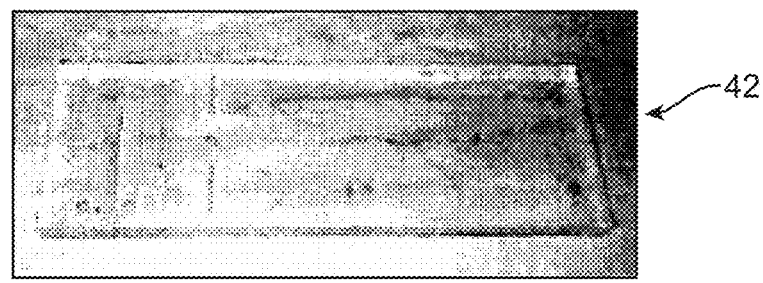
FIG. 5A
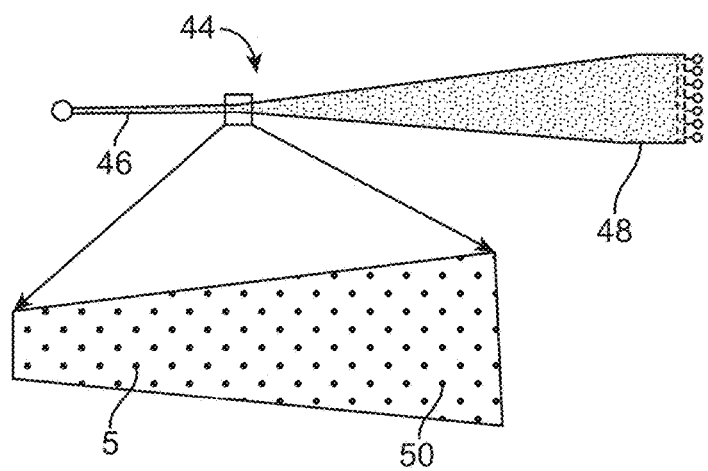
FIG. 5B
|  | FlowCount Fluorospheres (# of particles/µL) | Immunotrol High (# of cells/µL) | Immunotrol Low (# of cells/µL) |
|---|---|---|---|
| Flow Cytometer | 1007 ± 100 | 670 ± 70 | 158 ± 28 |
| ChipCare prototype | 970 ± 70 | 620 ± 15 | 184 ± 17 |
FIG. 6

METHODS AND DEVICES FOR CELL DETECTION

CROSS-REFERENCE

This application is a U.S. National Phase of PCT/IB2015/002084, filed Sep. 29, 2015, which claims the benefit of U.S. Provisional Application No. 62/056,718, filed Sep. 29, 2014, which is herein incorporated by reference.

BACKGROUND

Detection and quantification of microscopic particles in bodily fluids, such as white blood cells, bacteria, and viruses, as well as other analytes, such as proteins, enzymes and metabolites, is important in diagnosing and treating many conditions that impair human health. For example, identifying CD4 T-cell counts in patients provide physicians with information of the patient's HIV infection status. Healthcare providers often take multiple CD4 T-cell counts over time in order to determine the progression of the disease and the effectiveness of HIV treatments. A falling CD4 T-cell count indicates that HIV is progressing and damaging the immune system, whereas a rising CD4 T-cell count indicates that HIV treatments are altering the course of the disease.

SUMMARY

Traditional methods of detecting cells have included flow cytometry as a means for achieving high sensitivity and accuracy. Existing technologies require complex infrastructure and highly trained personnel. Conventional flow cytometry systems largely remain inaccessible for global routine clinical use, due to the size and cost of such systems. Additionally, some systems are capable of analyzing only one type of cell or particle, limiting the usefulness of such systems, particularly in resource poor settings and remote areas. Accordingly, provided herein are cartridges, detection modules, systems, and kits that offer superior cost effectiveness, portability, and usability as compared to currently available technology. The cell detection and analysis system is rugged, portable and compact, allowing for accurate and sensitive cell sample analysis in the field.

In one aspect, disclosed herein are methods and devices including a cartridge comprising: one or more housing units; a fluidic chip incorporating one or more microfluidic channel(s) that one or more particles or cells flows through within the fluidic chip; a detection window incorporated in one of the one or more housings, the detection window being operable to facilitate the capture of one or more images of one or more particles or cells flowing within the detection window. In some embodiments, the cartridge is a disposable cartridge. In some embodiments, the fluidic chip further comprises: a base, second, and capping layer; an inlet through which the sample is introduced to the microfluidic channel; an outlet through which the sample may be removed from the fluidic chip; and a waste reservoir positioned near the outlet, the waste reservoir being operable to collect the sample after the sample has flowed through the microfluidic chip.

In some embodiments, the cartridge includes features that drive fluid flow based on capillary forces or surface tension. In some embodiments, the features also support the overall structure of the cartridge, and may aid in filtering and preparation of the sample introduced into the cartridge. In some embodiments, the fluidic chip comprises posts or post structures positioned within the fluidic chip. In still other embodiments, the fluidic chip comprises patterned channels, optionally in a defined geometric or symmetrical pattern, or chambers to aid in mixing the sample and reagents in situ. In yet other embodiments, the fluidic chip comprises patterned channels in a non-symmetrical pattern. In still further embodiments, the fluidic chip further comprises a combination of posts and patterned channels.

In some embodiments, the cartridge includes features that drive fluid flow based on mechanical force. In further embodiments, the cartridge includes a bellow actuator, which drives the fluid flow through the cartridge. In further embodiments, the bellow actuator includes a micro stepper motor. In further embodiments, the bellow actuator includes a micro pump actuator. In further embodiments, the bellow actuator includes a micro pump actuator driver. In further embodiments, the bellow actuator aids in the mixing of the sample and reagents in situ. In yet further embodiments, the cartridge includes a combination of posts, patterned channels, and one or more bellow actuators to drive fluid flow.

In some embodiments, the fluidic chip and detection window are incorporated in one housing unit. In some embodiments, the cartridge connects to the detection module, and the detection module presents a sample analysis to a user. In some embodiments, the detection window and detection module are operable to apply multi-fluorescence detection. In some embodiments, sample preparation is integrated into the cartridge. In further embodiments, the cartridge including sample preparation is placed into a separate module for processing of the sample. In some embodiments, the sample preparation module comprises a plurality of slots for loading at least one or more cartridges for sample processing. The cartridge is then placed into an analyte detection module for detection. In some embodiments, sample preparation is incorporated into a separate device. In other embodiments, a sample preparation device and cartridge are placed into a housing and integrated together.

In some embodiments, all reagents required for the test are supplied and sealed in the cartridge. In further embodiments, the reagents are dried on the chip. In further embodiments, the reagents are lyophilized. In further embodiments, the reagents are slow dried. In further embodiments, the reagents on the cartridge have a shelf life of at least 12 months at 0° C. to 40° C., at least 12 months at 10° C. to 40° C., at least 12 months at 10° C. to 30° C., at least 12 months at 20° C. to 30° C., at least 12 months at 10° C., at least 12 months at 20° C., at least 12 months at 30° C., at least 12 months at 40° C. In further embodiments, the reagents on the apparatus have a shelf life of at least 48 hours with fluctuations between 0° C. and 50° C. In some embodiments, the cartridge holds a maximum volume of 200 microliters. In other embodiments, the cartridge holds a maximum volume of 100 microliters. In yet other embodiments, the cartridge may process a sample with a maximum volume of 100 microliters. In still other embodiments, the cartridge may process a sample with a maximum volume of 50 microliters. In further embodiments, the cartridge may process a sample with a maximum volume of 20 micro liters to 40 microliters. In some embodiments, the cartridge requires a minimum of 2 microliters for analysis. In some embodiments, the cartridge requires a minimum of 2 microliters to 15 microliters for analysis. In some embodiments, the cartridge requires a minimum of 2 microliters to 10 microliters for analysis. In some embodiments, the cartridge requires a minimum of 2 microliters to 5 microliters for analysis. In some embodiments, the cartridge has a system for metering the amount of blood to be analyzed.

In some embodiments, the metering system incorporates a software approach where the cell/particle speeds are measured as they are detected. After detection, their motion will be tracked as they move across the detection region. Given the speed measured and the microchannel dimensions (width and depth), the embedded image analysis software can calculate the volume processed by the detection system. In other embodiments, the metering approach incorporates a hardware-based approach. In some embodiments, two light detectors are placed in a waste collection channel downstream away from the detection region. The two light detectors are separated by a known distance, which dictates a certain amount of pre-determined volume. Once the sample front reaches the first detector, the embedded software starts the volume measurement, and when the sample front reaches the second detector, that means the pre-determined amount of sample has been processed and analyzed. Both examples described can accurately measure or calculate sample volumes processed on the microfluidic device.

In some embodiments, the cartridge contains an internal system that provides quality control and calibration for each test. In some embodiments, the cartridge has mechanical and optical markings for alignment. In some embodiments, the cartridge is marked with a unique identification number.

In another aspect, disclosed herein are detection modules, comprising: an optical imaging system; a cartridge loading mechanism; a bellow actuator; and an interconnection board. In some embodiments, the detection module further comprises: a display; a tracking tag reader; power system; an input/output connectivity; processing unit; wireless connectivity; and storage or memory. In some embodiments, the detection module further comprises a non-slip gripping surface. In some embodiments, the interconnection board comprises data storage; input/output mechanisms; and software. In further embodiments, the detection module further comprises a battery. In some embodiments, the battery is rechargeable. In further embodiments, the detection module further comprises a keyboard. In some embodiments, the detection module comprises a touchscreen. In some embodiments, the detection module is readable in direct sunlight. In some embodiments, the detection module dimensions do not exceed 24×13×8.5 cm. In some embodiments, the detection module uses visual and audible indicators to communicate to the user when a test is complete or has failed. In some embodiments, the detection module is capable of reading, displaying, and storing a date, time, operator ID, patient ID, site ID, cartridge ID, instrument ID, absolute and/or % CD4 T-cell count, white blood cell count, and quality control status, and combinations thereof. In some embodiments, the detection module may be disabled by a central data center. In some embodiments, the software maintains privacy standards equivalent to government regulatory standards, for example HIPAA or HL-7, when displaying, storing, and transmitting patient data. In some embodiments, the detection module's software can be updated or upgraded from a remote server. In some embodiments, the detection module can connect to a computer using input/output connectivity. In some embodiments, the input/output connectivity is through a USB port. In some embodiments, the detection module is capable of accepting a replaceable SIM card. In some embodiments, the detection module is capable of reading tracking tags, bar codes, or accepting information manually entered through a keyboard or touch screen.

In another aspect, disclosed herein are cell and particle detection and analysis systems, comprising: a cartridge containing a fluidic chip incorporating a microfluidic channel operable for one or more cells or particles to flow within the microfluidic channel; a detection module operable to capture one or more images of the one or more cells or particles flowing within the fluidic chip. In some embodiments, the fluidic chip incorporates a detection area and the detection module is operable to capture images of one or more cells or particles flowing within the fluidic chip through the detection window. In some embodiments, the optical source is a light source that is positioned either above or below the fluidic chip. In some embodiments, the detection module incorporates a CMOS detector or a CCD detector. In some embodiments, the system operates on a finger prick blood sample, heel stick blood sample, or from blood collected using a Vacutainer tube. In some embodiments, the system provides quantitative absolute CD4 T-cell, white blood cell count, and % CD4 T-cell measurements, and combinations thereof. In some embodiments, the system achieves >90% accuracy over the range of 50 to 3000 cells per microliter. In some embodiments, the system achieves >90% accuracy over the range of 100 to 1000 cells per microliter. In some embodiments, the system contains an internal quality control and calibration mechanism in each chip. In some embodiments, the detection module incorporates an image analysis program operable to analyze the one or more images captured by the detection module to produce analysis results. In further embodiments, the image analysis program produces diagnostic results. In some embodiments, the system is ruggedized. In some embodiments, the system is portable. In some embodiments, the fluidic chip, optical source, and detection module may be incorporated within a single housing. In some embodiments, the system is capable of performing at least 24 tests within an 8-hour period. In some embodiments, the system does not report a test if: there is insufficient amount of blood in the housing; there are air bubbles detected in the sample; the optical detector overheats; there is insufficient power to perform a complete test; or the test is run with an expired cartridge. In some embodiments, the system tolerates: transportation between 5° C. and 50° C.; storage between 5° C. and 30° C.; and non-condensing humidity range of 10-95% for operation, transportation, or storage. In some embodiments, the system is capable of communicating with a printer: wirelessly; or using input/output connectivity. In some embodiments, the input/output connectivity is through a USB port. In some embodiments, the system provides traceability of: the test procedure to the user ID; and the result to the test ID to the patient ID to the cartridge ID. In some embodiments, the system is operable to take static optical images of the sample inside the analysis chamber.

In another aspect, disclosed herein, is a product prepared by the process comprising the steps of introducing a sample of one or more cells or particles to a cartridge containing a fluidic chip; flowing the sample through a microfluidic channel within the fluidic chip; and operating a detection module to analyze the sample flowing within the fluidic chip. In some embodiments, the product prepared by the process further comprises the steps of: the detector module operating a detector to capture one or more images of the sample flowing past a detection window section of the fluidic chip; the detection module operating an images analysis program to analyze the one or more images; and the images analysis program generating results relating to the sample. In further embodiments, the product prepared by the process further comprises the step of the image analysis program generating diagnostic results relating to the sample. In some embodiments, the product prepared by the process further comprises the step of the detection module applying one or more calculations and one or more algorithms to analyze the sample. In some embodiments, the product prepare by the process further comprises the steps of creating a portable system, including a cartridge as disclosed herein that incorporates the fluidic chip and optical imaging module; and a user carrying the portable system, including a cartridge, to various locations to perform cell or particulate detection and analysis. In further embodiments, the product prepared by the process further comprises the step of carrying the portable device, including a cartridge as disclosed herein, to perform cell detection and analysis in one or more of the following: one or more remote locations; one or more developing locations; one or more developed locations. In some embodiments, the product prepared by the process further comprises the step of storing the analysis of the cell sample.

In another aspect, described herein, is a process of cell or particle detection and analysis, comprising introducing a sample of one or more cells or particles to a cartridge containing a fluidic chip; flowing the sample through a microfluidic channel within the fluidic chip; and a detection module to analyze the sample flowing within the fluidic chip. In some embodiments, the process further includes operating a detector to capture one or more images of the cell sample flowing past a detection window section of the fluidic chip; the detection module operating an image analysis program to analyze the one or more images; and the image analysis program generating cell analysis results relating to the cell sample. In further embodiments, the process further comprises the image analysis program generating results relating to the cell sample. In further embodiments, the process further comprises the detection module applying one or more calculations and one or more algorithms to analyze the cell sample. In further embodiments, the process further comprises creating a portable cartridge that incorporates the fluidic chip and optical imaging module; and a user carrying the portable cartridge to various locations to perform cell detection and analysis. In further embodiments, the process further comprises carrying the portable cartridge to perform cell detection and analysis in one or more of the following: one or more remote locations; one or more developing locations; one or more developed locations. In further embodiments, the process further comprises the step of storing the analysis of the cell sample.

In another aspect, disclosed herein, are kits comprising: one or more cartridges; one or more lancets; and one or more capillary tubes or pipettes. In some embodiments, the kit further comprises a detection module. In some embodiments, the kit's capillary tube or pipette is marked so as to ensure the correct amount of blood is collected and transferred to the disposable housing. In some embodiments, the kit's capillary tube or pipette is heparinized. In some embodiments, the kit's capillary tube is treated with EDTA.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features of the methods and devices disclosed herein are set forth with particularity in the appended claims.

A better understanding of the features and advantages of the present invention will be obtained by reference to the following detailed description that sets forth illustrative embodiments, in which the principles of the invention are utilized, and the accompanying drawings of which:

FIG. 5 shows a non-limiting example of (a) a microfluidic chip, (b) with an enlarged view of a cell detection and analysis microchip, in particular showing the posts.

FIG. 6 shows a non-limiting example of a table providing comparison of results of tests performed on a flow cytometer and a prototype device.

FIGS. 11A-11D show a non-limiting example of images (60) captured by an optical imaging system detector at: (FIG. 11A) 50 ms exposure; S/B 3/2; (FIG. 11B) 25 ms exposure, S/B 1300/900; (FIG. 11C) 15 ms exposure, S/B 750/550; (FIG. 11D) 10 ms exposure, S/B 695/500.

FIGS. 12A-12B shows a non-limiting example of: (FIG. 12A) a fluid flow speed of the sample (56) as flow velocity, and (FIG. 12B) filling time of the sample (58) as each lap time.

DETAILED DESCRIPTION

Figures 1A, 1B:
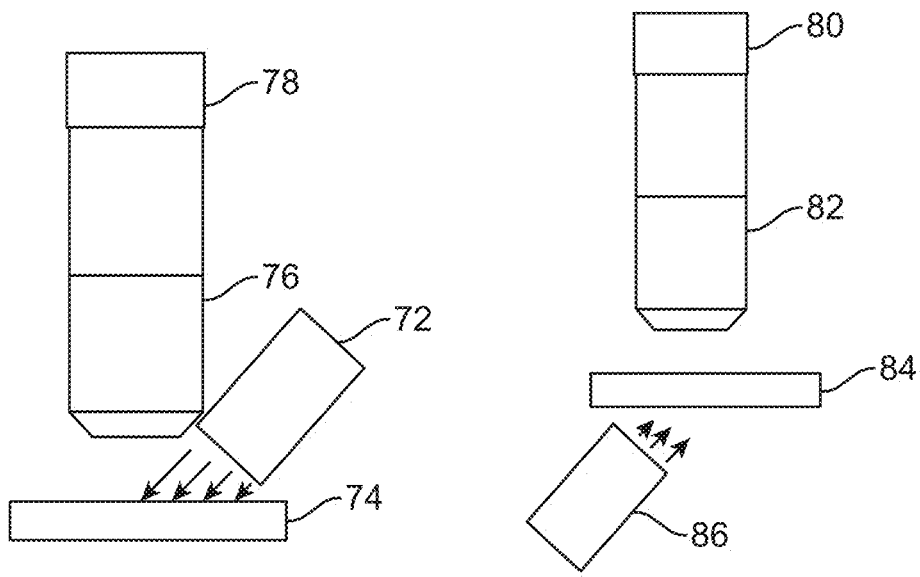
FIG. 1 shows non-limiting examples of optical imaging system configurations, wherein the light source is directed to the (a) top or (b) bottom edge of the disposable cartridge.

Flow cytometry is a technique used in the field of particle detection and identification. Typically, flow cytometer instruments require complex infrastructure and highly trained personnel. The use of flow cytometry in the clinic is limited due to the size and cost of such systems. Advantages of the cartridge, detection module, system, and kit described herein include, but are not limited to, providing a simpler, more compact, cost effective, and portable particulate detection and analysis system. Further advantages of the cartridge, detection module, system, and kit described herein include having the sample flow over the detection module, which allows the detection module to remain in the same position, precluding necessary repositioning of a chip, sample, or filter. Still further advantages of the cartridge, detection module, system, and kit described herein include diminished clumping of particulates, scaling capabilities to analyze many different types of particulates, and continuous image capturing capabilities.

Described herein, in certain embodiments is a cartridge for cell or particulate detection and analysis comprising: one or more housing units; a fluidic chip incorporating a microfluidic channel that one or more cells or particles of a sample flows through within the fluidic chip; a detection window incorporated in one of the one or more housings, the detection window being operable to facilitate the capture of one or more images of one or more cells or particles flowing within the detection area.

Also described herein, in certain embodiments, are detection modules comprising: an optical imaging system; a cartridge loading mechanism; a bellow actuator; and an interconnection board.

Also described herein, in certain embodiments, is a cell or particle detection and analysis system comprising: a cartridge containing a fluidic chip incorporating a microfluidic channel operable for one or more cells or particles to flow within the microfluidic channel; a detection module operable to capture one or more images of the one or more cells or particles flowing within the fluidic chip.

Also described herein, in certain embodiments, is a process of cell or particle detection and analysis, comprising the steps of: introducing a sample of one or more cells or particles to a cartridge containing a fluidic chip; flowing the sample through a microfluidic channel within the fluidic chip; and a detection module to analyze the sample flowing within the fluidic chip.

Also described herein, in certain embodiments, are kits, comprising: one or more cartridges; one or more lancets; and one or more capillary tubes for sample collection.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise noted.

Analysis

In some embodiments, the devices, cartridges, detection modules, systems, and kits described herein include cell and particle detection and analysis. In further embodiments, "cell" or "cells" may include all types of cellular material, including but not limited to human cells, e.g., white blood cells, whole blood cells, lymphocytes and other cells derived from a human, animal cells, microbial cells, including but not limited to bacteria, fungal or viral cells. In some embodiments, "particles" may include all organic and inorganic particles and particulate matter, with different shapes, sizes, chemical and biological modifications, including but not limited to cellular debris, cell membranes, organelles, synthetic beads or particles, and other particles or particulates or combinations thereof. In further embodiments, the particles may include organic compounds such as, but not limited to, proteins, enzymes, metabolites, vitamins, carbohydrates and/or fats. In further embodiments, the particles may include a drug or other medicine. In further embodiments, the particles may include allergens, such as, but not limited to pollen, spores, dust, and dander.

In further embodiments, the cell or particle detection and analysis devices, systems and methods described herein are operable to achieve white blood cell analysis. In some embodiments, the cell and particle sample detection and analysis devices and methods disclosed herein are operable to detect HIV, hepatitis B, hepatitis C, syphilis, sepsis, malaria and other indications or diseases. In other embodiments, the cell and particle sample detection and analysis devices and methods disclosed herein are capable of detecting food and water-borne pathogens. In yet other embodiments, the cell and particle sample detection and analysis devices and methods disclosed herein are capable of quantifying creatinine and viral load for HIV/AIDS. In still other embodiments, the cell detection and analysis devices and methods disclosed herein are operable to achieve CD4 T-cell analysis and counting. In further embodiments, the cell and particle sample detection and analysis devices, systems and methods described herein may be operable to achieve other types of analysis and counting, for example, such as analysis and counting of CD3, CD8, CD64, CD4 or CD45 cells. Also, in some embodiments, the cartridges, detection modules, systems, and kits described herein may be operable to be used for tracking and counting cells or particles with sizes from about 1 micron to 100 microns in diameter. In further embodiments, the particles may be submicrons. In various embodiments, the cells or particles may be less than 10, 20, 30, 40, 50, 60, 70, 80, 90, or 100 microns. In yet other embodiments, the cells or particles may be more than 1, 10, 20, 30, 40, 50, 60, 70, 80, 90 or 100 microns.

In some embodiments, the sample comprises bodily fluid, whole blood, blood, serum, plasma, cerebrospinal fluid, body tissue, urine or saliva, sputum, water, milk or other fluidic samples. In other embodiments, the sample is from a human, an animal, a plant, an insect, or a cell culture. In other embodiments, the sample is from a food, a beverage, a growth medium, an environmental sample, a liquid, water, or a combination thereof.

Housing Units

In some embodiments, the devices, cartridges, detection modules, systems, and kits described herein include a housing unit, or use of the same. In further embodiments, the housing unit is formed out of any suitable housing material, for example, but not limited to, a plastic or metal material, or combination of the same. In further embodiments, the size and shape of the housing may vary with the configuration of the cartridge.

Fluidic Chip

In some embodiments, the devices, cartridges, detection modules, systems, and kits described herein include a fluidic chip, or use of the same. In further embodiments, the fluidic chip may be a fluidic cartridge, a microfluidic cartridge, a microfluidic chip, or some other applicable element. In yet further embodiments, the fluidic chip may contain a base layer, a second layer, and a capping layer. In other embodiments, the fluidic chip may contain a base and capping layer. In some embodiments, the base layer may incorporate fluidic structures, for example, but not limited to, structures defined in a SU-8 negative photoresist, plastic, acrylic, or polymer material. In further embodiments, the fluidic channels may be patterned using a photolithography technique such that the depositing step may involve spin coating and drying techniques, or hot embossing/injection molding. In other embodiments, the base layer may have lengths ranging from 1 to 300 mm and width ranging from 1 to 200 mm. In some embodiments, the base layer may comprise glass, polymer, metal, semiconductor material such as silicon, or combinations of the same. In yet further embodiments, the base layer may be fully cured. In some embodiments, the second layer may be deposited by the same steps as used to deposit the base layer. In further embodiments, the second layer may be further patterned, such as, but not limited to, exposing through a photomask. In some embodiments, the second layer may have lengths ranging from 1 to 300 mm, and width ranging from 1-200 mm. The other embodiments, the second layer may comprise glass, polymer, photoresist, or mixtures thereof. In some embodiments, the capping layer may be made of a variety of materials, such as, but not limited to plastic acrylic. In further embodiments, the capping layer may be partially cured SU-8 photoresist layer deposited with mechanically drilled holes to form inlets and outlets. In some embodiments, a housing is included to protect the fluidic cartridge. In other embodiments, the housing may be made a polymer material, such as plastic acrylic, using an injection molding process. In some embodiments, the housing also allows ease of use for the user to handle the cartridge.

In some embodiments, the fluidic chip may incorporate one or more areas, such as a sample loading compartment, a mixing chamber, a fluidic channel, and an analysis chamber. In further embodiments, the fluidic chip may contain a sample loading compartment, where the sample is transferred by pipette into a port. In further embodiments, the sample loading compartment is treated with EDTA. In further embodiments, the sample loading compartments is treated with heparin or other anti-coagulant. In some embodiments, the cartridge accommodates a blood sample, for example from a finger prick collected using a pipette. In some embodiments, from about 1 to about 100 microliters, from about 1 to about 50 microliters, from about 1 to about 25 microliters, from about 1 microliters, from about 5 microliters, from about 10 microliters, from about 15 microliters, from about 20 microliters, from about 25 microliters, from about 30 microliters, from about 35 microliters, from about 40 microliters, from about 45 microliters, from about 50 microliters, from about 55 microliters, from about 60 microliters, from about 65 microliters, from about 70 microliters, from about 75 microliters, from about 80 microliters, from about 85 microliters, from about 90 microliters, from about 95 microliters, from about 100 microliters will be transferred to the microfluidic cartridge using the pipette. In another embodiment, the microfluidic cartridge can have a sample collection port where a blood sample, for example from a finger prick, can be directly collected and loaded on to the cartridge.

In yet further embodiments, the sample loading compartment requires a cap, plug, or seal. In some embodiments, the sample loading compartment comprises a cap, plug or seal as disclosed in PCT/EP2014/064290, which is incorporated in its entirety herein. In still further embodiments, the sample loading compartment is hermetically sealed. In still other embodiments, the fluidic chip may contain a mixing chamber, where the sample may be mixed with reagents. In yet other embodiments, the mixing chamber may contain slow-dried or freeze dried reagents. In further embodiments, the reagents are lyophilized. In still other embodiments, the cap, plug, or seal may be coated with or contain reagents for mixing in situ within the cartridge. In yet further embodiments, the mixing chamber may contain fluorescently labelled antibodies. In some embodiments, the mixing chamber may contain antibodies coated onto beads. In yet other embodiments, the antibodies coated onto beads may be fluorescently labeled. In yet further embodiments, the mixing chamber is a passive fluidic mixer and may be contained within the preparation chamber or analysis chamber. In still further embodiments, the fluid within the mixing chamber may be mixed using a bellows-actuated system.

In some embodiments, the fluidic chip may contain a fluidic channel, where the channel may include a narrow interrogation region that may be designed to create a laminar flow of cells or particles. In further embodiments, the fluidic chip may contain a plurality of microfluidic channels. In some embodiments, the fluidic channel interrogation region may be less than 1500 microns, less than 1200, less than 900 microns, less than 800 microns, less than 700 microns, less than 600 microns, less than 500 microns, less than 400 microns, less than 300 microns, less than 200 microns, or less than 100 microns wide. In other embodiments, the fluidic channel interrogation region may be from about 400 microns to about 1000 microns wide. In yet other embodiments, the fluidic channel interrogation region may be from about 500 to about 700 microns wide. In still other embodiments, the fluidic channel interrogation region may be 100 to 1000 microns wide. In some embodiments, the fluidic channel interrogation region may be 600 microns wide. In other embodiments, the fluidic channel interrogation region may be less than 2000 microns, less than 1800 microns, less than 1600 microns, less than 1500 microns, less than 1400 microns, less than 1300 microns, less than 1200 microns, less than 1100 microns, less than 1000 microns, less than 800 microns, less than 600 microns long. In some embodiments, the fluidic channel interrogation region may be from about 800 to about 1600 microns long. In still other embodiments, the fluidic channel interrogation region may be from about 1000 to about 1400 microns long. In further embodiments, the interrogation region may be approximately 1-50 microns, less than 10 microns, less than 20 microns, less than 30 microns, less than 40 microns, or less than 50 microns deep. In yet further embodiments, the interrogation region may be greater than 10 microns, greater than 20 microns, greater than 30 microns, greater than 40 microns, or greater than 50 microns deep. In yet further embodiments, the fluidic channel interrogation region. In further embodiments, the interrogation region may be defined by the size of the detection module.

In some embodiments, the microfluidic channel may include one or more posts. In further embodiments, the microfluidic channel posts may be a variety of sizes and/or in a variety of shapes, including but limited to a square, a circle, a rectangle, or a hexagon. In some embodiments, the posts could be glass, polymer, photoresist or combinations thereof. In other embodiments, the microfluidic channel posts may be positioned at regular, uniform intervals within the channel, or may be randomly spaced. In further embodiments, the posts may be 1-200 microns in width, including posts less than 10, 20, 30, 40, 50, 60, 70, 80, 90, 100, 110, 120, 130, 140, 150, 160, 170, 180, 190, or 200 microns wide, including any width therein. In yet further embodiments, the posts may be may be more than 1, 10, 20, 30, 40, 50, 60, 70, 80, 90, 100, 110, 120, 130, 140, 150, 160, 170, 180, 190, or 200 microns wide, including any width therein. The posts may be of different heights to separate layers of the chip. The posts may be used to keep the cells or particles from clumping. In some embodiments, the posts are used to separate cell or particulate sizes, and/or to drive fluid flow in the fluidic and mixing channel.

In some embodiments, the microfluidic channel may be a patterned channel. In further embodiments, the pattern may be a curved pattern. In further embodiments, the pattern may be a straight pattern. In further embodiments, the pattern may be a serpentine pattern. In further embodiments, the pattern may be a meandering pattern. In further embodiments, the pattern may be a "u" pattern. In further embodiments, the pattern may be a "w" pattern. In further embodiments, the pattern may be a "c" pattern. In further embodiments, the pattern may be a microvascular pattern. In further embodiments, the pattern may be a zigzag pattern. In further embodiments, the patter may be a geometric pattern.

In some embodiments, the microfluidic channel may take the form of various geometrical or patterned shapes. In further embodiments, the microfluidic channel may be a cylindrical channel. In further embodiments, the microfluidic channel may be oval. In further embodiments, the microfluidic channel may be triangular. In further embodiments, the microfluidic channel may be square. In further embodiments, the microfluidic channel may be rectangular. In further embodiments, the microfluidic channel may be spindle-shaped. In further embodiments, the microfluidic channel may be an irregularly shaped. In further embodiments, the microfluidic channel may be custom shaped. In further embodiments, the microfluidic channel may be "v" shaped.

In some embodiments, the fluidic chip may contain an analysis chamber, where the sample moves into and fills up the analysis chamber. In further embodiments, sample entry into the analysis chamber may be filled once the entire sample has entered the analysis chamber, or before the sample has entered the analysis chamber. In further embodiments, the analysis chamber may trigger the optical detector in the detection module to start capturing images. In yet further embodiments, once the entire analysis chamber is completely filled, the optical detector's image capturing process may stop and the captured images may then be combined for analysis.

In some embodiments, the fluidic chip may include a sample introduction inlet, a sample preparation chamber, a particle analysis chamber, a detection window, and a waste reservoir. In further embodiments, the inlets and chambers are connected so that the introduction inlet is connected to the preparation chamber, so that cells or particles introduced to the cartridge may flow from the introduction inlet through the preparation chamber to the analysis chamber and through the analysis chamber to the waste reservoir. In yet other embodiments, the waste reservoir may be incorporated as disclosed in EP2437890, which is incorporated herein in its entirety. In still further embodiments, the waste chamber is connected to the preparation chamber. In yet further embodiments, the cells or particles collected in the waste reservoir may be disposed of through removal of the waste reservoir. In still further embodiments, the waste reservoir is reattachable. In further embodiments, the waste reservoir may contain a disposable container. In still further embodiments, the waste reservoir itself is disposable. In still further embodiments, the cells or particles may be removed from the waste reservoir without detaching the waste reservoir, for example, but not limited to, flushing or aspiration of the sample.

In some embodiments, the flow of fluid within the fluidic chip may be driven by capillary force. In some embodiments, the flow of fluid within the fluidic chip may be driven by mechanical force. In further embodiments, the flow of fluid within the fluidic chip may be driven by a bellow actuator. In further embodiments, the flow of fluid within the fluidic chip may be a laminar flow. In further embodiments, the fluidic chip may be disposable. In still further embodiments, the fluidic chip may be made of glass or polymer substrates, such as, but not limited to, plastic acrylic. In yet further embodiments, the fluidic chip may be made from hot embossing or injection molding techniques. In some embodiments, the fluidic chip may be fabricated using a photolithography technique.

Detection Window

In some embodiments, the cartridges, detection modules, systems, and kits described herein include a detection window, or use of the same. In further embodiments, the detection window allows for the optical detector to capture images of cells or particles flowing into or through the analysis chamber. In yet further embodiments, the detection window may be comprised of one or more optical filters; here, the optical filters may be adhered to the top surface of the detection window or a coating may be provided on an independent transparent optical element that may be positioned in front of the window section, or the filters are placed in front of the detector. In some embodiments, the transparent window may be made from material with excellent optical properties such as transparent polymer, or glass. In other embodiments, there is no magnification factor associated with the filters. In yet other embodiments, the filter is a fluorescence emission filter. In some embodiments, the ranges of the emission filters are 585/40 nm, 670/40 nm, 650 long pass filter, or 708/75 nm. In some embodiments, the detection window may be positioned under, over, or upon a portion of the disposable cartridge, or under, over, or upon the whole of the cartridge. In still further embodiments, the detection window may incorporate the same color optical filter two or more times. This may be used to calculate an average as the cell sample passes by the detection window. In a further embodiment, the detection channel can pass through the detection window. Additional filters can be added to the detection window to detect other emission wavelengths to accomplish simultaneous detection of multiple fluorescence wavelengths.

Detection Module and Optical Detector

In some embodiments, the devices, cartridges, systems, and kits described herein include a detection module, or use of the same. In further embodiments, the detection module may optionally include an optical imaging system, a cartridge loading mechanism, a processing unit, a bellow actuator, an interconnection board, a power system, and/or a display.

Optical Imaging System

In some embodiments, the cartridges, detection modules, systems, and kits described herein include an optical imaging system, or use of the same. In further embodiments, the optical imaging system may include an optical source, optical detector, and lens components. In some embodiments, the detection module may include free space integrated with the optical detector. In further embodiments, the detection module may include a free space optical filter. In yet further embodiments, the detection module may include one or more integrated detectors. In some embodiments, the components are stand-alone devices or instruments. In yet other embodiments, the detection system may optionally include optical lenses. For example, in some embodiments a CCD/CMOS camera, microscope objective lens, light source, and filters are assembled mechanically without integration or optimization. In further embodiments, the optical imaging system may optionally include mirrors. In yet further embodiments, the mirrors may be comprised of fused silica and aluminum. In some embodiments, the optical imaging system may optionally include a photodiode.

In further embodiments, the optical imaging system may not include any moving components, such as, but not limited to, filter wheels and rotation stages. In some embodiments, the optical imaging system may capture one or more static optical images.

Optical Source

In some embodiments, the cartridges, detection modules, systems, and kits described herein include an optical source, or use of the same. In further embodiments, the optical source may be a light illuminating source. In some embodiments, the light illuminating source may be a laser diode or light emitting diode device. In still further embodiments, the light source may be a fiber optic light source. In further embodiments, the fiber optic light source may include a light guide. In still further embodiments, the optical source may be a free space or fiber/light guide coupled with or otherwise connected to the optical source. In yet further embodiments, the optical source may be, located above or below the cartridge, but is not limited to these two locations. In some embodiments, the optical source may also include a free space optical filter and/or a Bragg grating filter that may be integrated in the fiber/light guide. In further embodiments, the optical source may include an optical detector. In yet further embodiments, the optic light delivery may be coated with an excitation filter.

Optical Detector

In further embodiments, the detection module may be an image acquisition and analysis module that may include an optical detector. In still further embodiments, the optical detector may be a variety of types, for example, a charge coupled device (CCD) image sensor, or a complementary metal oxide semi-conductor (CMOS) image sensor. In further embodiments, the CCD or CMOS sensor may have an active sensing area diagonal width of 0.5 mm or less, 1 mm or less, 2 mm or less, 3 mm or less, 4 mm or less, 5 mm or less, 6 mm or less, 7 mm or less, 8 mm or less, 9 mm or less, 10 mm or less, 15 mm or less, 20 mm or less, 30 mm or less, 40 mm or less, 50 mm or less, 60 mm or less, 70 mm or less, 80 mm or less, 90 mm or less or 100 mm or less. In still further embodiments, the CCD or CMOS sensor may have an active sensing area diagonal width of 0.5 mm or more, 1 mm or more, 2 mm or more, 3 mm or more, 4 mm or more, 5 mm or more, 6 mm or more, 7 mm or more, 8 mm or more, 9 mm or more, 10 mm or more, 15 mm or more, 20 mm or more, 30 mm or more, 40 mm or more, 50 mm or more, 60 mm or more, 70 mm or more, 80 mm or more, 90 mm or more, or 100 mm or more. In further embodiments, the optical detector may possess a resolution of at least 1 megapixel, at least 2 megapixels, at least 3 megapixels, at least 4 megapixels, at least 5 megapixels, at least 6 megapixels, at least 7 megapixels, at least 8 megapixels, at least 9 megapixels, at least 10 megapixels, or more. In yet further embodiments, a CCD sensor may take the dimensions of a 3 mm×0.5 mm rectangular sensor, or the CCD sensor may have an active detection area of approximately 10.2 mm×8.3 mm. In yet further embodiments, the CCD sensor may be, but is not limited to, a CCD camera such as Pixelfly USB. In some embodiments, the optical detector may capture optical images over time, at regular or irregular intervals. In some embodiments, the optical detector is coated with one or more emission filters, where the coating may be a direct coating, or an independent optical element that may be positioned in front of the window section of a fluidic chip. In still further embodiments, the optical detector may incorporate multiple emission filters in a single window. In some embodiments, the filter shape is a circle, half-moon shaped, rectangle, or square. In still further embodiments, the optical detector may include one or more dichroic filters. In some embodiments, the detection region is separated into two sub regions to detect fluorescence. In further embodiments, the optical detector may not include either an emission filter or any dichroic mirrors. In still further embodiments, the optical detector may contain optical filters for fluorescence emission collection, including, but not limited to, long wave pass, broad band, 585/40, 670/40, and 708/75 filters. In further embodiments, the optical detector may contain a custom designed emission filter. In further embodiments, the optical detector may be further divided up into a number of small sub-regions, and each sub-region may be coated with an optical filter. In further embodiments, each sub-region may detect or otherwise highlight one particular color or fluorochrome, as a result of the optical filter. In yet further embodiments, two or more independent fluorescence images may be superimposed, to create a multi-color fluorescence cytometry system.

Lens

In some embodiments, the optical imaging system may include a lens. In further embodiments, the lens is a magnification lens, for example a three element telescopic 5×, 7×, 10×, 20× or other suitable optical lenses, or other lens. In still further embodiments, the lens is an off-the-shelf microscope objective lens. In still further embodiments, the lens may be a microscope objective lens, such as, but not limited to, 4× NA 0.1 objective lens, a 10× NA 0.25 objective lens, a 10× NA 0.30 objective lens, or other suitable objective lens configuration. In yet further embodiments, the lens may be positioned above or below a disposable cartridge. In further embodiments, the lens may be an optical lens tube assembly. The magnification lens may magnify the targeted cells or particles and may project these cells or particles onto an optical detector.

Cartridge Loading Mechanism

In some embodiments, the devices, cartridges, detection modules, systems, and kits described herein include a cartridge loading mechanism. In some embodiments, the cartridge loading mechanism may include a sliding reference pin. In other embodiments, the cartridge loading mechanism may include a rotating camshaft. In yet other embodiments, the cartridge loading mechanism may include a linear cam. In some embodiments, the cartridge loading mechanism includes two plungers. In further embodiments, the plunger is designed with a parallel blade mechanism. In yet further embodiments, the plunger includes a stainless steel reference ball. In yet further embodiments, the plunger mechanism may include wave washers. In further embodiments, the cartridge loading mechanism may include openings for finger access. In some embodiments, the cartridge loading mechanism may include a door. In further embodiments, the door may be sealed via, for example, but not limited to, a gasket mechanism. In further embodiments, the cartridge loading mechanism may position the fluidic chip vertically or horizontally, but is not limited to these two positions.

Bellow Actuator

In some embodiments, the devices, cartridges, detection modules, systems, and kits described herein include a bellow actuator. In further embodiments, the bellow actuator includes a micro stepper motor. In further embodiments, the bellow actuator includes a micro pump actuator. In further embodiments, the micro pump actuator may include either mechanical and/or non-mechanical micro pumps. In further embodiments, the micro pump may be, but is not limited to a magneto hydro dynamic micro pump, electro hydrodynamic micro pump, electro-osmotic micro pump, DC electro-osmotic micro pump, AC electro-osmotic micro pump, electro wetting micro pump, bubble-type micro pump, or electrochemical micro pump. In further embodiments, the micro pump actuator may be, but is not limited to, an electrostatic, piezoelectric, thermo-pneumatic, shape memory alloy, bimetallic, ion conductive polymer film, or electromagnetic actuation method.

In some embodiments, the bellow actuator includes a micro pump actuator driver. In further embodiments, the micro pump actuator driver is connected to the interconnection board. In further embodiments, the micro pump actuator driver may connect to the interconnection board by way of an inter-integrated circuit (I2C), subscriber identification module (SIM), universal serial bus (USB), ADS, general-purpose input/output (GPIO), flash LED output, secure digital input/output (SDIO), high speed inter-chip (HSIC), pulse width modulation (PWM), pulse code modulation (PCM), serial peripheral interface (SPI), controller area network (CAN), TxBURST indicator, or 1-WIRED interface, but is not limited to these options. In some embodiments, the micro pump actuator driver may possess, ¼, ⅛, ¹⁄₁₆, or ¹⁄₃₂ step microstepping, but is not limited to any of these options. In some embodiments, the micro pump actuator driver may possess a wide power supply voltage range, for example, but not limited to, 1 volt to 15 volts. In some embodiments, the micro pump actuator driver may be adjusted by a serial digital-to-analog converter. In some embodiments, the micro pump actuator driver may contain an encoder. In further embodiments, the micro pump actuator driver may contain a limit switch.

Interconnection Board

In some embodiments, the devices, cartridges, detection modules, systems, and kits described herein include an interconnection board. In some embodiments, the interconnection board may include a computer-on-module (COM), system-on-module (SOM), and/or system-on-chip (SOC). In further embodiments, the COM, SOM, and/or SOC may connect to system components by way of an inter-integrated circuit (I2C), subscriber identification module (SIM), universal serial bus (USB), ADS, general-purpose input/output (GPIO), flash LED output, secure digital input/output (SDIO), high speed inter-chip (HSIC), pulse width modulation (PWM), pulse code modulation (PCM), serial peripheral interface (SPI), controller area network (CAN), TxBURST indicator, or 1-WIRED interface, but is not limited to these options.

In some embodiments, the COM, SOM, and/or SOC may possess at least 1 MB, at least 10 MB, at least 100 MB, at least 1000 MB, at least 1 GB, at least 10 GB, at least 100 GB, or at least 1 TB of memory storage. In further embodiments, the COM, SOM, and/or SOC may possess at least 1 MB, at least 10 MB, at least 100 MB, at least 1000 MB, at least 1 GB, at least 10 GB, or at least 100 GB of random-access memory.

In some embodiments, the interconnection board includes provisions for system monitoring. In further embodiments, system monitoring may convey laser temperature. In further embodiments, system monitoring may convey laser power. In further embodiments, system monitoring may convey system temperature. In further embodiments, system monitoring may include a status LED on the interconnect board. In further embodiments, system monitoring may include a LED to indicate the device is powered. In further embodiments, system monitoring may include a status LED on the outside of the device, cartridge, detection module, system, or kit described herein. In further embodiments, system monitoring may include a self-vibrating piezo buzzer on the interconnect board. In further embodiments, system monitoring may include a real-time clock. In further embodiments, the clock has a battery backup so it keeps track of time even when the device is not in operation.

Software

In some embodiments, the cartridges, detection modules, systems, and kits described herein include software, or use of the same. In some embodiments, the software is located on the interconnection board. In other embodiments, the software is located on an external computer. In further embodiments, the software may be an image analysis program. In further embodiments, the image analysis program may utilize the images captured by the optical detector. In further embodiments, the image analysis program may be used to detect intensity levels in the samples. In further embodiments, the image analysis program may be used to analyze and process the acquired optical images for particle and cell detection and enumeration. In further embodiments, the image analysis program includes an algorithm, and the algorithm may be applied to any number of characteristics, including, but not limited to, motion analysis of cells or particles flowing through the detection window, or statistical data of the entire sample. In still further embodiments, the image analysis program includes a two-phase analysis, by which the first step includes collecting a set of images generated during a specified time period and the second step includes collecting and analyzing the images as a group. In yet further embodiments, image analysis occurs in real time, as the cells or particles pass through the detection window; in this embodiment it is not necessary to collect a set of images before beginning an analysis step. In some embodiments, the image analysis program is configured to achieve multiplexed analysis. In further embodiments, the image analysis program may track the location of fluorescently labelled subjects by way of a virtual bounding box, whereby the minimum and maximum x and y coordinates of each cell or particle may be identified and recorded by the imaging analysis program. In further embodiments, the image analysis program may count cells or particles upon entrance and exit of the detection window area. In further embodiments, the image analysis program may store analyzed images internally or externally to a device. In yet further embodiments, storage means may be lined or otherwise connected to a device by way of a wired or wireless connection.

Display

In some embodiments, the devices, cartridges, detection modules, systems, and kits described herein include a display. In further embodiments, the display is connected to the interconnection board through an inter-integrated circuit (I2C), subscriber identification module (SIM), universal serial bus (USB), ADS, general-purpose input/output (GPIO), flash LED output, secure digital input/output (SDIO), high speed inter-chip (HSIC), pulse width modulation (PWM), pulse code modulation (PCM), serial peripheral interface (SPI), controller area network (CAN), TxBURST indicator, or 1-WIRE® interface, but is not limited to these options. In further embodiments, the display can be configured so that all functions are controllable by software. In further embodiments, the display may measure at least 1 inch, 2 inches, 3 inches, 4 inches, 5 inches, 6 inches, 7 inches, 8 inches, 9 inches, 10 inches, or more diagonally. In further embodiments, the display may have an input voltage of at least 0.5 volts, 1 volt, 2 volts, 3 volts, 4 volts, 5 volts, 10 volts, 15 volts or more. In further embodiments, the display may be located above, to the side, or below the cartridge insertion door, or in any configuration convenient for the user. In further embodiments, the display may be connected to or independent of the devices, cartridges, and detection modules described herein. In further embodiments, the display may be connected to or independent of the keyboard. In yet further embodiments, the display may include a virtual keyboard. In further embodiments, the display may be a touchscreen.

Tracking Tag Reader

In some embodiments, the devices, cartridges, detection modules, systems, and kits described herein include a tracking tag reader. In some embodiments, the reader is able to read/decode one dimensional or two dimensional barcodes. In further embodiments, the reader is able to read, for example, but is not limited to, codabar, code 25, code 11, code 39, code 49, code 93, code 128, CPC binary, DX film edge barcode, EAN2, EAN 5, EAN-8, EAN-13, Facing Identification Mark, GS1-128, GS1 DataBar, Intelligent Mail barcode, ITF-14, JAN, KarTrak ACI, MSI, Pharmacode, PLANET, Plessey, PostBar, POSTNET, RM4SCC, Telepen, UPC, microPDF, PDF417, Aztec Code, Code 1, ColorCode, Color Construct Code, CrontoSign, CyberCode, d-touch, DataGlyphs, DataMatrix, digital paper, EZcode, High Capacity Color Barcode, Han Xin Barcode, HueCode, InterCode, MaxiCode, MMCC, NexCode, PDF417, Qode, QRcode, ShotCode, microQR, or SPARZCode. In some embodiments, the reader may be able to read/decode radio-frequency identification (RFID) tags. In further embodiments, the reader may include, but is not limited to, a passive reader active tag (PRAT) system, an active reader passive tag (ARPT) system, and/or an active reader active tag (ARAT) system. In some embodiments, the tracking tag reader is a Bluetooth reader. In further embodiments, the tracking tag reader may be a GPS or satellite tracking reader. In further embodiments, the tracking tag reader may include, but is not limited to, a hardwired GPS tracking device, a GPS Logger, personal GPS trackers, and/or real-time GPS trackers.

In some embodiments, the tracking tag reader may connect to the interconnection board through an inter-integrated circuit (I2C), subscriber identification module (SIM), universal serial bus (USB), ADS, general-purpose input/output (GPIO), flash LED output, secure digital input/output (SDIO), high speed inter-chip (HSIC), pulse width modulation (PWM), pulse code modulation (PCM), serial peripheral interface (SPI), controller area network (CAN), TxBURST indicator, or 1-WIRE® interface, but is not limited to these options.

Power System

In some embodiments, the devices, cartridges, detection modules, systems, and kits described herein include a power system. In further embodiments, the power system includes a battery. In some embodiments, the battery may be a non-rechargeable battery. In further embodiments, the non-rechargeable battery may include such types, but is not limited to, an alkaline, aluminum-air, atomic, dry cell, galvanic cell, lithium, lithium-air, mercury, nickel oxyhydroxide, organic radical, paper, silver-oxide, solid state, water-activated, zinc-air, or a zinc-carbon battery. In some embodiments, the battery may be a rechargeable battery. In further embodiments, the non-rechargeable battery may include such types, but is not limited to a, flow, aluminum-ion, lithium-ion, lead-acid, nickel-cadmium, nickel-hydrogen, nickel-metal hydride, nickel-zinc, organic radical, polymer-based, polysulfide bromide, potassium-ion, rechargeable alkaline, rechargeable fuel, silicon-air, silver-zinc, silver calcium, sodium-ion, sodium-sulfur, sugar, super-iron, or an ultra-battery. In some embodiments, the battery is located below the optical source or optical detector, to create a handle. In further embodiments, the battery is located behind the optical source or optical detector, to create a rectangle product. In further embodiments, the battery may be positioned in any orientation convenient for the user.

In some embodiments, the power system contains a battery charger. In further embodiments, the battery charger may include such types, but is not limited to, supplying a simple constant DC or pulsed DC power source, fast chargers, inductive chargers, intelligent chargers, linear chargers, low power charger, motion-powered chargers, pulse chargers, SMBus charger, solar chargers, stand-alone charger, switch-mode chargers, timer-based chargers, trickle chargers, universal battery charger-analyzers, USB-based chargers, wireless chargers, or powerbanks.

In some embodiments, the power system contains a wall plug adapter. In further embodiments, the wall plug adapter may be earthed, polarized, fused, and/or possess insulated pins. In further embodiments, the wall plug adapter may include, but is not limited to, a plug and socket type A, type B, type C, type D, type E, type F, type G, type H, type, I, type J, type K, type L, type M, type N, or type O plug and socket type. In further embodiments, the wall plug adapter may be a USB connector. In further embodiments, the wall plug adapter may be low profile, standard, or swivel. In further embodiments, the wall plug adapter may be suited for low voltage power outlets. In further embodiments, the wall plug adapter may be suited for high voltage power outlets. In further embodiments, the wall plug adapter contains a wall mount power supply, which may, but is not limited to, output power greater than 1 watt, greater than 5 watts, greater than 10 watts, greater than 15 watts, greater than 25 watts, greater than 35 watts, greater than 45 watts, greater than 55 watts, greater than 65 watts, greater than 75 watts, greater than 85 watts, or greater than 100 watts. In further embodiments, the wall plug adapter contains a wall mount power supply, which may, but is not limited to, output power less than 5 watts, less than 10 watts, less than 15 watts, less than 25 watts, less than 35 watts, less than 45 watts, less than 55 watts, less than 65 watts, less than 75 watts, less than 85 watts, or less than 100 watts.

Wireless Connectivity

In some embodiments, the devices, cartridges, detection modules, systems, and kits described herein include the capability for wireless connectivity. In further embodiments, the wireless connectivity may be, but is not limited to, Bluetooth technology, Wi-Fi technology, sub-1 GHz technology, 6LoWPAN technology, ZigBee technology, Z-Wave technology, RF4CE technology, NFC/RFID technology. In further embodiments, the wireless connectivity is part of a greater network, such as, but not limited to, a personal area network (PAN), a local area network (LAN), a metropolitan area network (MAN), a wide area network (WAN), sensor networks, cellular networks, or the internet. In further embodiments, cellular networks may include, but are not limited to, GSM, IS-95, UMTS, W-CDMA, EDGE, CDMA2000, or LTE technologies.

In some embodiments, some of the components which may be needed for wireless connectivity include an antenna, modem or module, SIM card, and/or server. In further embodiments, the antenna may be, but is not limited to, a cellular signal booster, a directional cellular antenna, an omni-directional cellular antenna, a Wi-Fi antenna, or combination antennas. In further embodiments, the module may be a wireless modem. In further embodiments, the module may be a 1G, 2G, 3G, or 4G module, but is not limited to these options. In further embodiments, the module is connected to an interconnection board. In further embodiments, the module is optionally connected to the interconnection board through a UART interface or through another interface based on UART technology. In further embodiments, the module is optionally connected to the interconnection board through an inter-integrated circuit (I2C), subscriber identification module (SIM), universal serial bus (USB), ADS, general-purpose input/output (GPIO), flash LED output, secure digital input/output (SDIO), high speed interchip (HSIC), pulse width modulation (PWM), pulse code modulation (PCM), serial peripheral interface (SPI), controller area network (CAN), TxBURST indicator, or 1-WIRE® interface, but is not limited to these options. In further embodiments, the module uses AT commands to send and receive information. In further embodiments, the module can be disabled either by software or with a discrete line.

Input/Output Connectivity

In some embodiments, the devices, cartridges, detection modules, systems, and kits described herein includes input/output connectivity. In further embodiments, the input/output connectivity may include USB connectivity. In further embodiments, the devices, cartridges, detection modules, systems, and kits described herein may connect to a computer by way of, but not limited to, type A, type B, mini-A, mini-AB, mini-B, micro-AB, micro-B, USB 3.0 type A, USB 3.0 type B, USB micro-B, type C, or other USB plug type. In further embodiments, the input/output connectivity may include Ethernet, SFF, Infiniband, USB, PCM-CIA, and/or HDMI, but is not limited to these options.

Keyboard

In some embodiments, the devices, cartridges, detection modules, systems, and kits described herein include a keyboard. In further embodiments, the keyboard may be a mechanical, membrane, dome-switch, scissor-switch, capacitive, mechanical-switch, buckling-spring, hall-effect, laser, roll-up, optical, or virtual keyboard. In further embodiments, the keyboard can be implemented as a scan matrix. In further embodiments, the keyboard may appear on the display. In further embodiments, the keyboard may be located above, to the side, or below the cartridge insertion door, but is not limited to these positions.

Internal Quality Control and Calibration System

In some embodiments, the cartridges, detection modules, systems, and kits described herein include an internal quality control and calibration system, or use of the same. In further embodiments, the internal quality control and calibration system may consist of commercially available beads. In still further embodiments, the internal quality control and calibration system may include alignment beads, cell counting beads, compensation beads, performance tracking beads, reference beads, or size calibration beads. In some embodiments, the beads are coated with a dye, including but not limited to phycoerythrin (PE), PE-Cy5, PE-Cy7, Pacific blue, Cascade blue, Brilliant violet, APC, nanoparticles, gold nanoparticles, quantum dots, and other suitable dyes or nanoparticles. In yet further embodiments, the internal quality control and calibration system may include phycoerythrin (PE) (excitation/emission 532 nm/585 nm) and PE-Cy5 (excitation/emission 532 nm/700 nm) labelled beads, 1-10 microns in diameter. In alternative embodiments, the fluorescent dyes are injected into the beads. In some embodiments, the internal quality control and calibration mechanism may incorporate saline, for example, such as 1× phosphate-buffered saline (PBS). In further embodiments, the internal quality control and calibration mechanism may consist of control cells, such as, but not limited to immunotrol.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the methods described herein.

Example 1—Cartridges for Detecting and Analyzing Cells or Particles

FIGS. 1, 2, 3, 4, and 5 provide non-limiting examples of possible configurations of the methods and embodiments disclosed herein.

FIG. 1 shows non-limiting configuration variations of the optical imaging system. FIG. 1a shows one embodiment, including an optical detector (78), lens (76), disposable cartridge (74), and light source (72), in which the light source (72) is positioned above the disposable cartridge (74) and angled to provide light to the upper surface of the disposable cartridge (74). FIG. 1b shows an alternative embodiment, including an optical detector (80), lens (82), disposable cartridge (84), and light source (86), in which the light source (86) is positioned beneath the disposable cartridge and may be angled to provide light to the underside of the disposable cartridge (84) below the lens (82).

Figure 2:
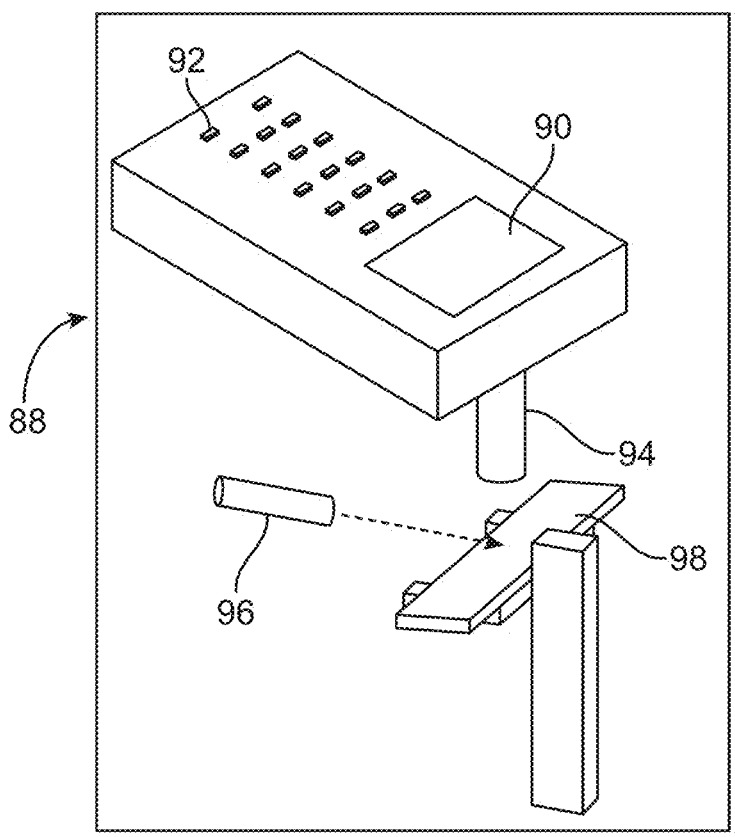
FIG. 2 shows a non-limiting example of an embodiment, including the optical imaging system and cartridge as they relate to the handheld device.

FIG. 2 is a non-limiting example of possible components that may be found within a single housing, or in the alternative, some components may be internal and others external to a housing. The components may include, but are not limited to a/an: housing (88), display (90), keyboard (92), optical imaging system (94), light source (96), and cartridge (98).

Figure 3:
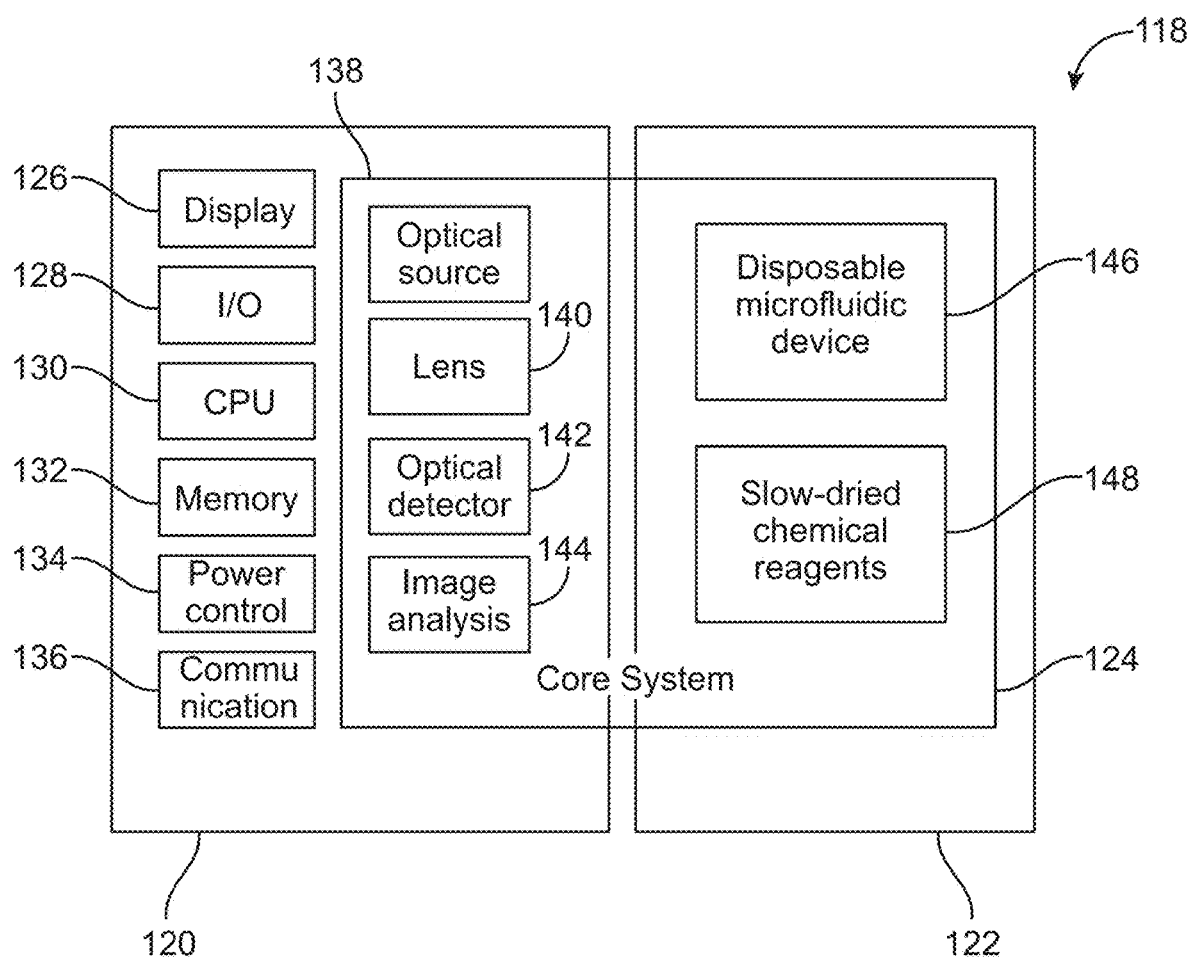
FIG. 3 shows a non-limiting example of the components incorporated within two or more cartridges, for example an analysis cartridge and a cartridge.

FIG. 3 is a non-limiting example of possible components of the claimed system (118), including an analysis cartridge (120) and a cartridge (122). A core system (124) may connect the analysis device (120) and the cartridge (122) through a wired or wireless connection. As shown in FIG. 3, elements of the core system may be incorporated in either the analysis device or the cartridge, for example, a/an: optical source (138), lens (140), optical detector (142), image analysis program or system (144), microfluidic cartridge (146), and reagents (148). The analysis device may also contain a display (126), input/outputs (128), CPU (130), memory (132), power control (134), and means of communicating with an external server (136).

Figure 4:
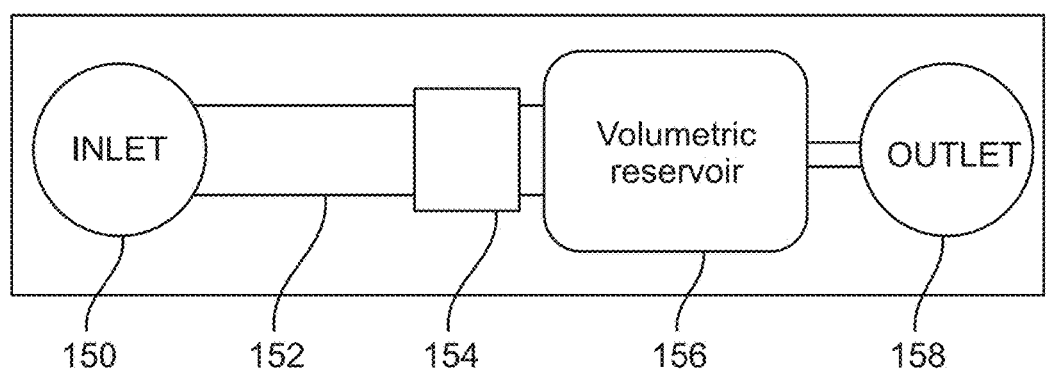
FIG. 4 shows a non-limiting example of components of the fluidic chip.

FIG. 4 is a non-limiting example of possible components of a fluidic chip described herein. The components may include, but are not limited to a/an: inlet (150), microfluidic channel (152), detector window (154), reservoir (156), and outlet (158).

FIG. 5 depicts non-limiting examples of components of the microfluidic chip (42). The microfluidic chip (42) may contain a microfluidic channel (44) with an interrogation region (46), which produces laminar flow of the sample. Beyond the detection point, the channel may widen (48) in order to reduce the fluidic resistance and improve flow speed. Additionally, the microfluidic channel may include one or more posts (5, 50), which may be a variety of sizes and may be positioned at regular intervals or randomly spaced throughout the channel.

Example 2—Flow Cytometer Comparison

Enumeration measurements were conducted on 6-um polymer microspheres, conjugated with phycoerythrin (PE) dyes, in phosphate buffered saline (PBS) solutions. The initial experiments were performed on an Olympus BX50 upright fluorescence microscope. Band pass filter sets were used for fluorescence excitation and emission measurements. An average count of 1007 particles/uL was obtained, while the flow cytometer produced a count of 970 particles/uL using the same sample.

The comparison involved the measurement of CD4 T-cell concentration in a whole blood sample. The microfluidic chips were tested using immunotrols, which were stabilized blood samples used to calibrate flow cytometer systems, at both high and low concentrations. The same fluorescent dyes were used in testing the stabilized blood sample. The testing produced an average count of 620 cells per microliter whereas the flow cytometer measured 670 cells per microliter. Results from a comparison between a conventional flow cytometer (62) and prototype of one embodiment (64) are shown in FIG. 6.

Figure 7:
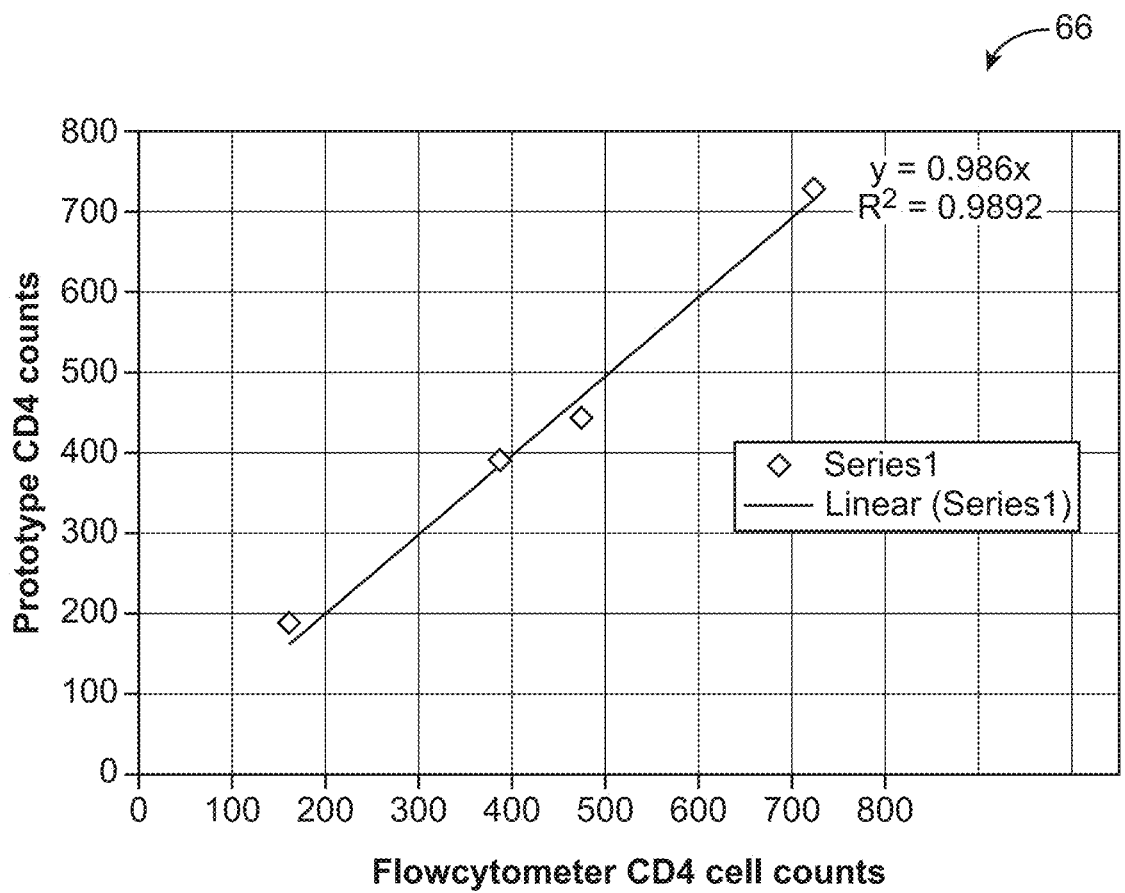
FIG. 7 shows a non-limiting example of a linearity test providing comparison of results of tests performed on a flow cytometer and prototype device.
Figure 8A:
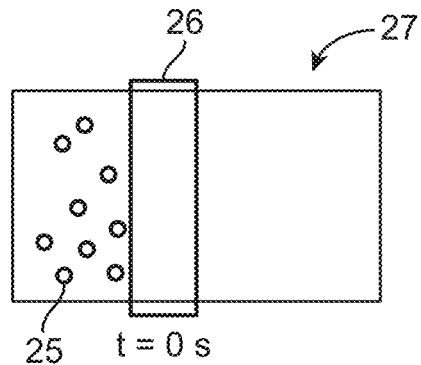
FIG. 8 shows a non-limiting example of a series of images captured at successive points in time. T=0 denotes the start of the image (0 seconds), and T=1, T=2, T=3, T=4, T=5, indicate 1, 2, 3, 4, and 5 seconds, respectively.
Figure 8D:
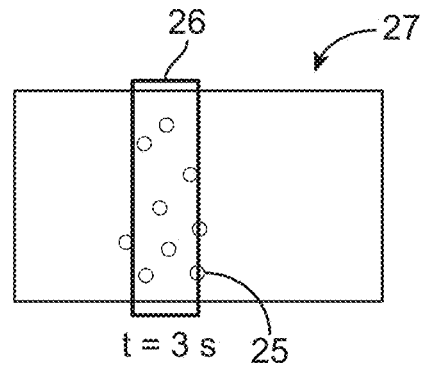
Figure 8B:
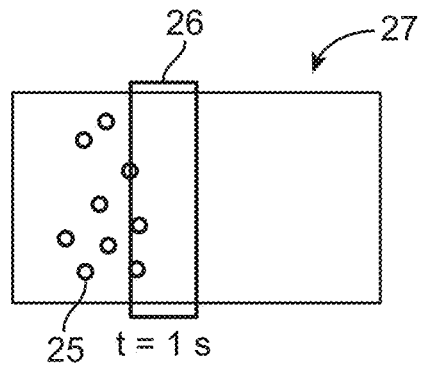
Figure 8E:
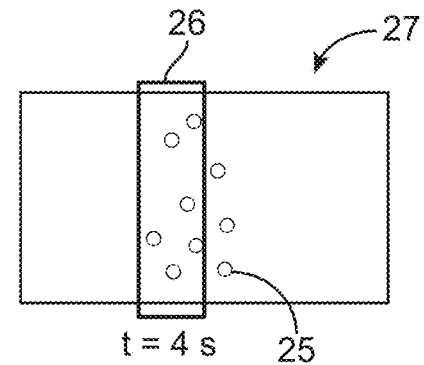
Figure 8C:
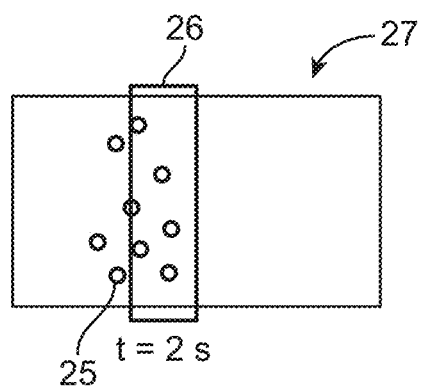
Figure 8F:
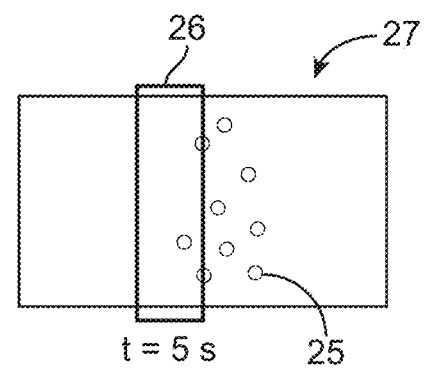

A linearity test was also performed to show the differences between a conventional flow cytometer and a cartridge embodiment. Results of the test are shown in the table of FIG. 7 (66). A range of cell populations of interest to CD4 enumeration assay was tested on a platform, from 150 per uL to 720 per uL, as shown in FIG. 7. The measurements were done in direct comparison to the conventional clinical flow cytometers, and were conducted over a range of cell populations of clinical relevance. The results of the comparison yielded a 98.6% agreement between two measurements. (Each data point shown in the table of FIG. 7 (66) is the average of the counting results obtained for that range.)

Example 3—Cell Detection Illustrations

Figure 9A:
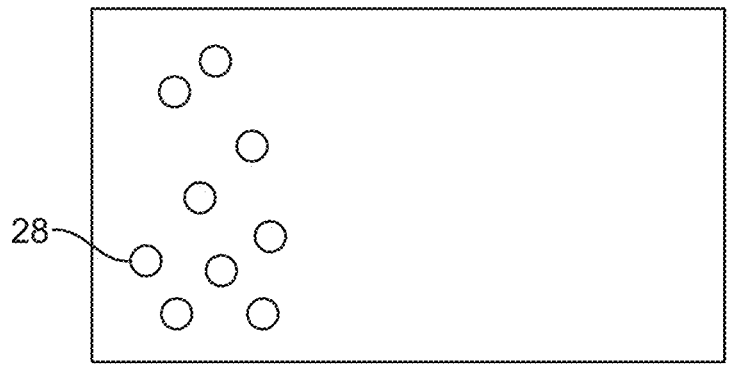
FIG. 9 shows a non-limiting example of cell or particulate movement inside the analysis chamber.
Figure 9B:
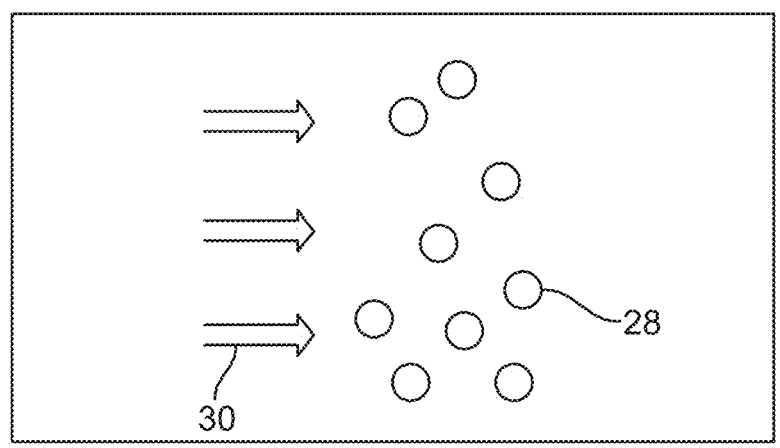
Figure 10:
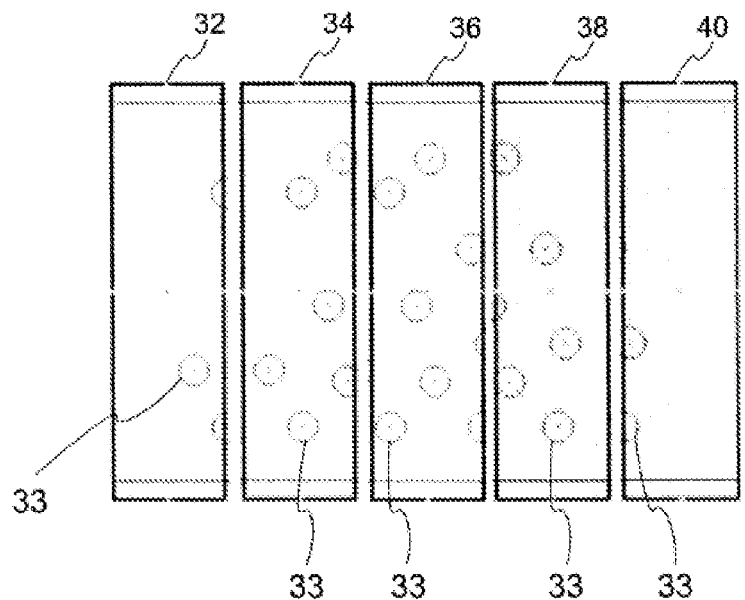
FIG. 10 shows a non-limiting example of a combined set of images generated by a CCD detector.

FIGS. 8, 9, and 10 show non-limiting illustrations of cell detection. FIGS. 8a-8f represent a time series of cells (25) moving through the detection window (26) on the microfluidic chip (27). In this example, t=0 s denotes the start of the image acquisition, where t equals zero seconds. FIGS. 8b-8f show the cells moving through the detection window at 1, 2, 3, 4, and 5 seconds, respectively. While the time series depicts images captured in 1 second intervals, the detector may capture images at any interval during the analysis stage. FIGS. 9a and 9b depict the flow (30) of cells (28) through the analysis chamber, whereby FIG. 9a depicts cells before beginning to flow (e.g. t=0 seconds), and FIG. 9b depicts the cells flowing at a later point in time (e.g. t=5 seconds). While the figures show cell flow from left to right within the chamber, the cell may flow in a variety of directions according to the design of the fluidic chip. FIG. 10 shows that cell (33) images (32, 34, 36, 38, and 40) may be combined together by the image acquisition and analysis module. Devices may be configured to capture images with or without redundancy. Redundancy within the images may improve cell detection accuracy.

Example 4—Flow Speed Optimization and Characterization

Figure 11A:
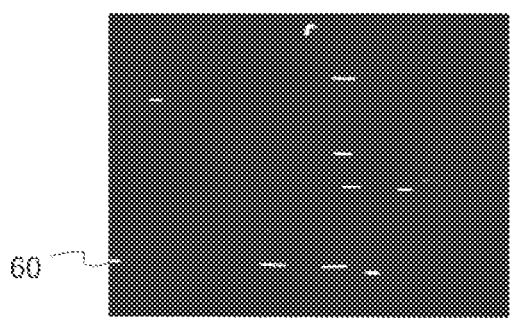
Figure 11B:
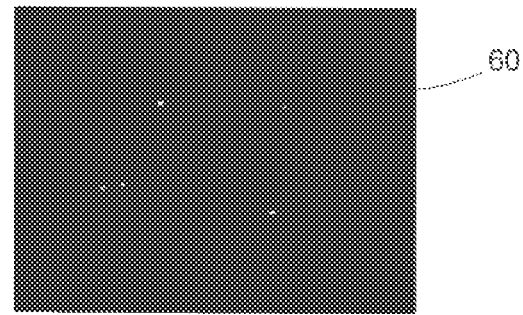
Figure 11C:
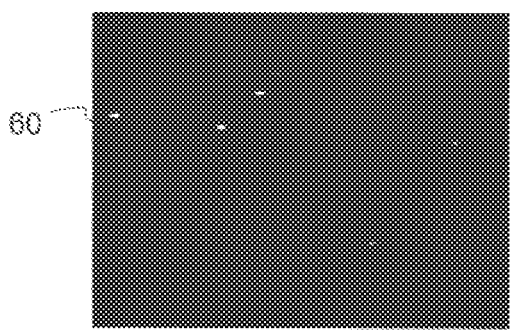
Figure 11D:
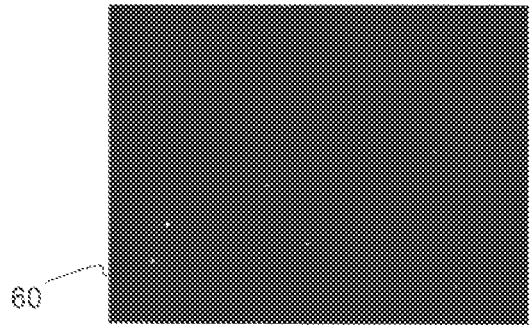
Figure 12A:
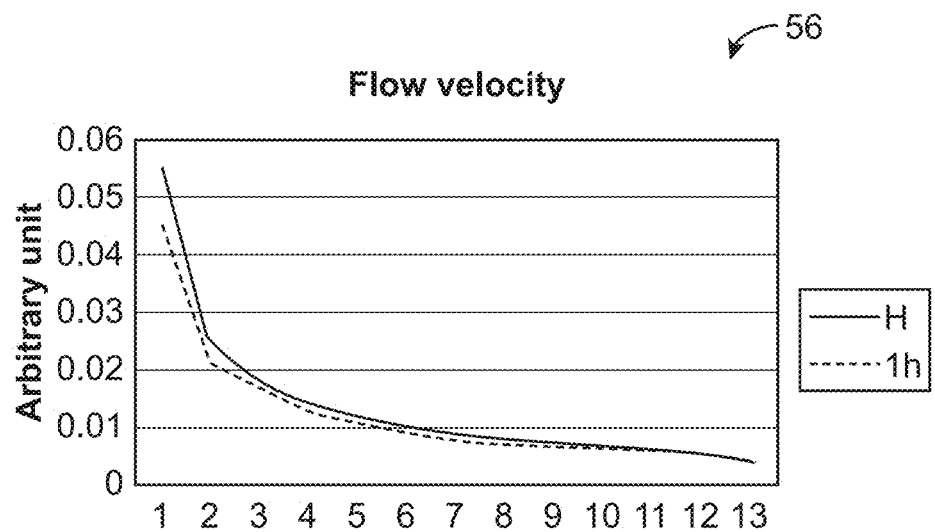
Figure 12B:
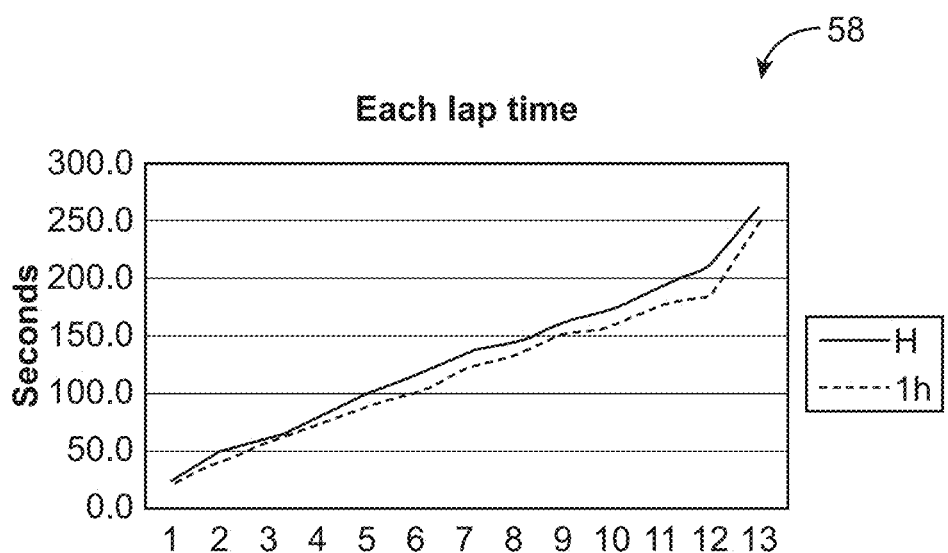

A large signal to noise ratio may be achieved by optimizing the optical detector, which may be an important parameter in achieving counting accuracy. If the integration time of the detector is too short, the fluorescence signal captured by the detector may be low and may compromise the signal to background ratio. On the other hand, if the integration time is too long, the cells in the sample may be travelling too fast for the detector to capture an image of such cells. If cells flow by and are not captured in an image by the detector, and therefore are not registered, this may lead to counting errors and errors in the analysis results. The optimal integration time of the devices and methods disclosed herein should allow the fluorescently labeled cells in the sample to produce sufficient signal, compared with the background noise. The electronic circuitry that drives the detector should also be fast enough to capture all the cells with a proper sampling rate. An example of the effect of the optical imaging system's detector exposure time is shown in FIGS. 11a-11d. FIG. 11a shows an image at a 50 ms exposure, S/B: 3/2. FIG. 11b shows an image at a 25 ms exposure, S/B: 1300/900. FIG. 11c shows an image at a 15 ms exposure, S/B: 750/550. FIG. 11d shows an image at a 10 ms exposure, S/B: 695/500. A comparison of FIGS. 11a-11d shows the signal to background ratio is lower at a shorter exposure, and that the cell's shape (shown as light shapes within the dark background in the images) appears more circular at a shorter exposure. Dynamic counting may be used to determine cell particle statistics. For example, the data from FIGS. 11a-11d may be plotted to show flow velocity representing the fluid flow speed, as shown in FIG. 12a, or the plotting may show each lap time representing the channel filling time, as shown in FIG. 12b. The plotting shown in FIGS. 12a and 12b correspond to the serpentine microfluidic chip structure shown in FIGS. 5a and 5b. Thus, a numerical model may be created before the microfluidic chip design occurs.

Example 5—Analysis of Two Color Imaging

Figure 13:
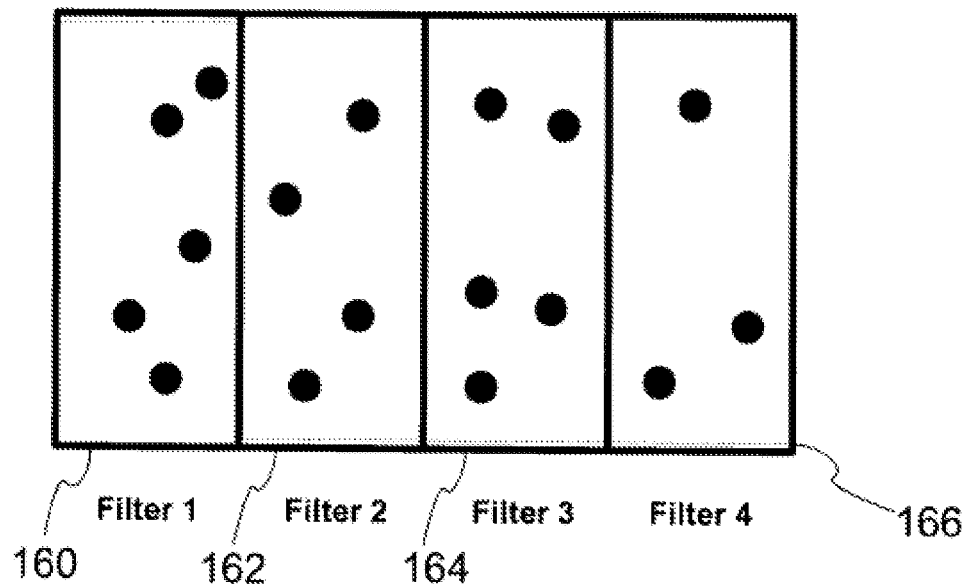
FIG. 13 shows a non-limiting example of multi-color fluorescence detection, wherein each filter provides color detection functionality.
Figure 14:
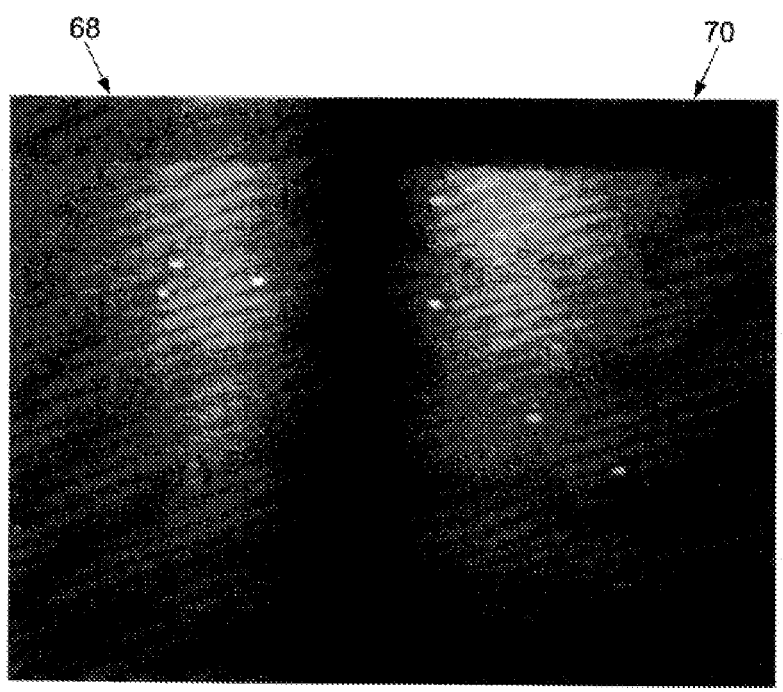
FIG. 14 shows a non-limiting example of a two color fluorescence image captured by an embodiment that incorporates two half-moon shaped optical filters placed together side-by-side in the optical imaging system.
Figure 15A:
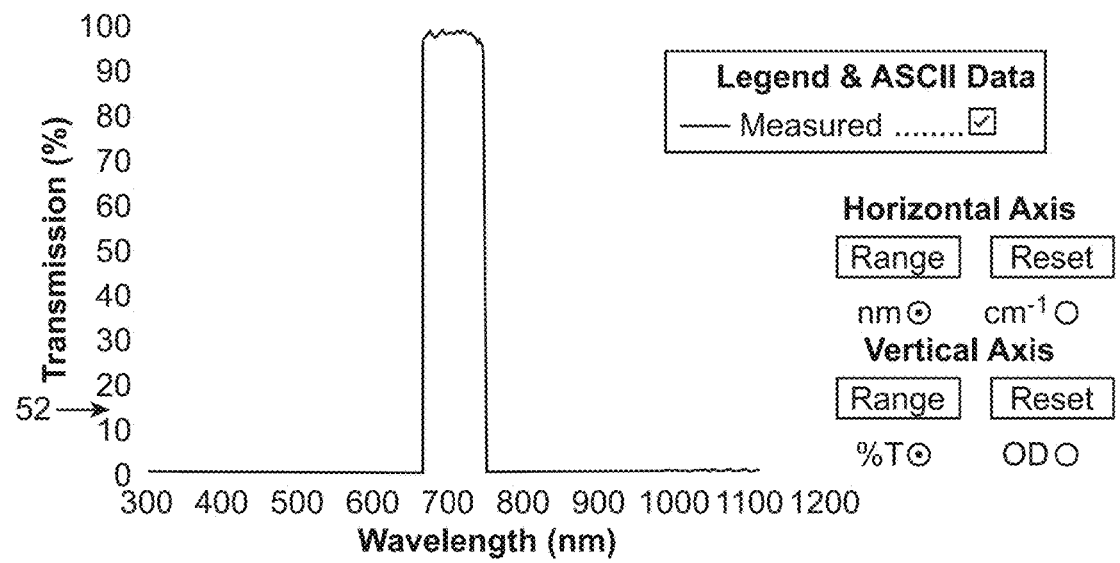
FIG. 15 shows a non-limiting example a transmission spectrum of two half-moon shaped filters.
Figure 15B:
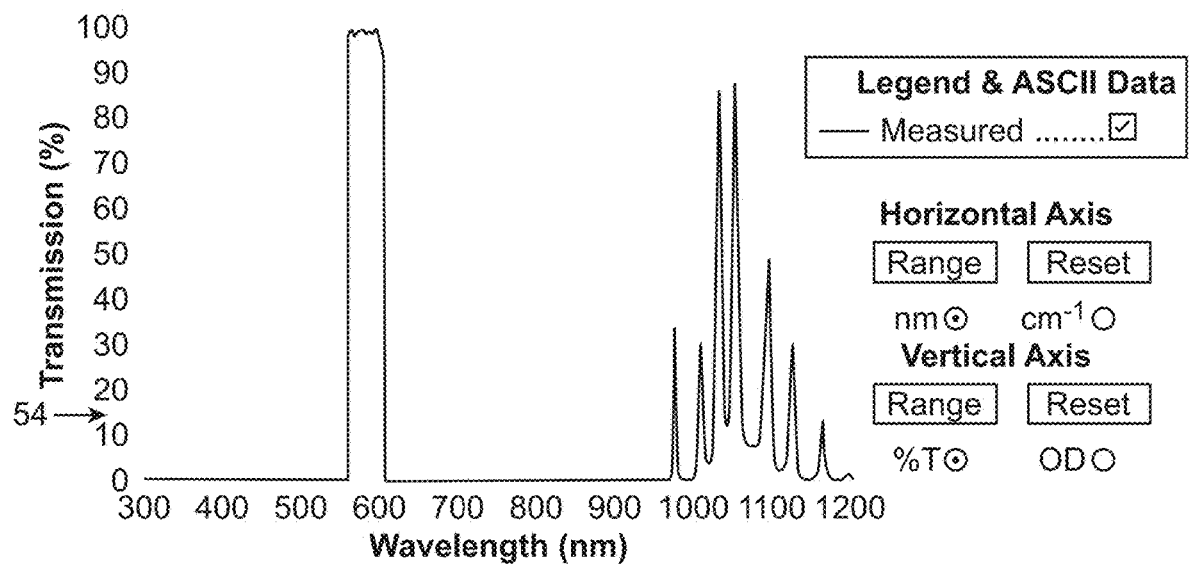
Figure 16:
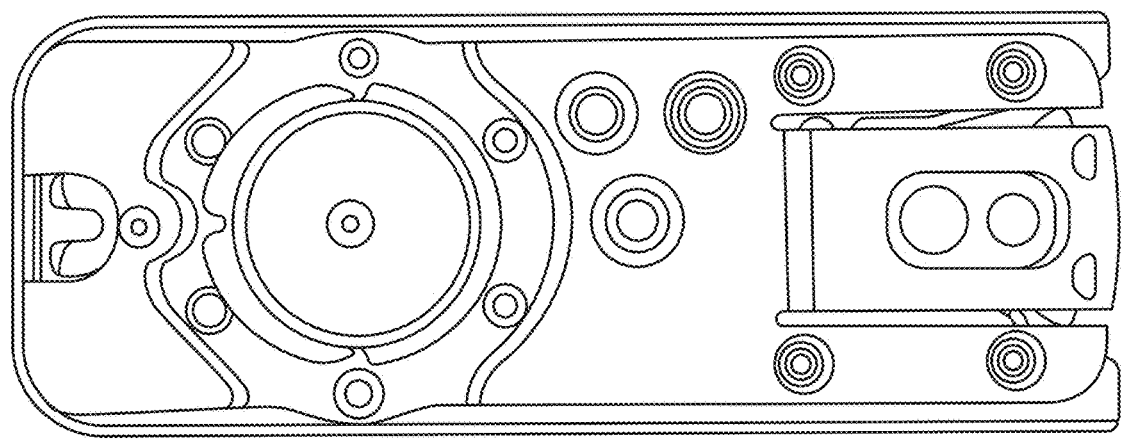
FIG. 16 shows a non-limiting example of a cartridge according to the methods and embodiments disclosed herein.

A user performs single or multi-colored imaging. Through multiple color imaging, the optical imaging system and software exhibits multiplexing capabilities, generating statistics of an individual cell group population and differential statistics of multiple cell types. In one example, as shown in FIG. 13, the user may analyze the data using four different fluorescence conjugated antibodies, in which the multi-color functionality is detected by incorporating four filters (160, 162, 164, and 166) or an arrayed filter in front of the optical detector. In another example, the user selects two fluorescent dyes, each conjugated to a specific cell, such that CD4 T-cells are tagged with PE dye while CD45 cells are labelled with PE-Cy5 molecules. Images captured by the optical imaging system and displayed through the image analysis software, show the detection of the sample, as captured by the PE (green, 68) and PE-Cy5 (red, 70) wavelengths (FIG. 14). By comparing the two images, the user measures the labelled cells. In yet another example, the user may analyze the data as transmission spectrums of the filter used, as shown in FIGS. 15a and 15b. The spectrum in FIG. 15a (52) represents the filter set output of measured ASCII data, whereas the spectrum in FIG. 15b (54) represents the filter set output of average ASCII data. The horizontal axis relating to both FIGS. 15a and 15b is for wavelength, as measured in nm, and a reset to $cm^{-4}$, and the vertical axis is the percentage of transmission, and a reset to OD.

Example 6—On-Chip Mixing Structures

Figure 17:
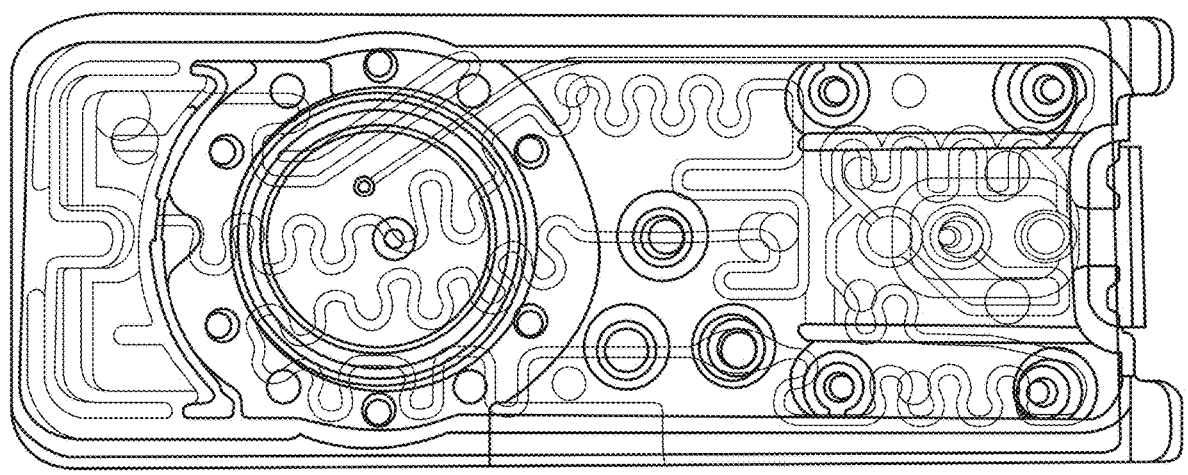
FIG. 17 shows a non-limiting example of a cartridge according to the methods and embodiments disclosed herein.
Figure 18:
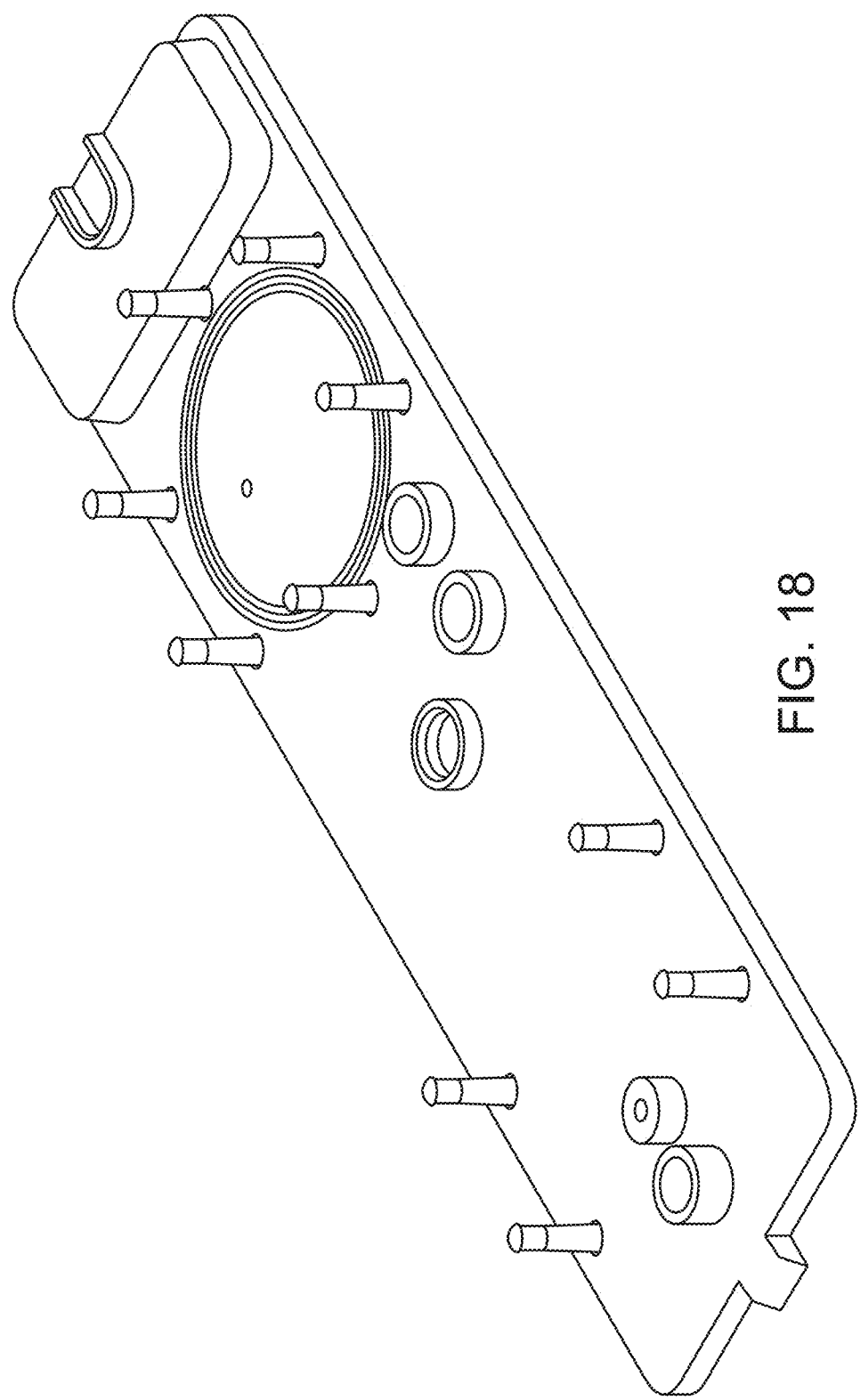
FIG. 18 shows a non-limiting example of a cartridge according to the methods and embodiments disclosed herein.
Figure 19:
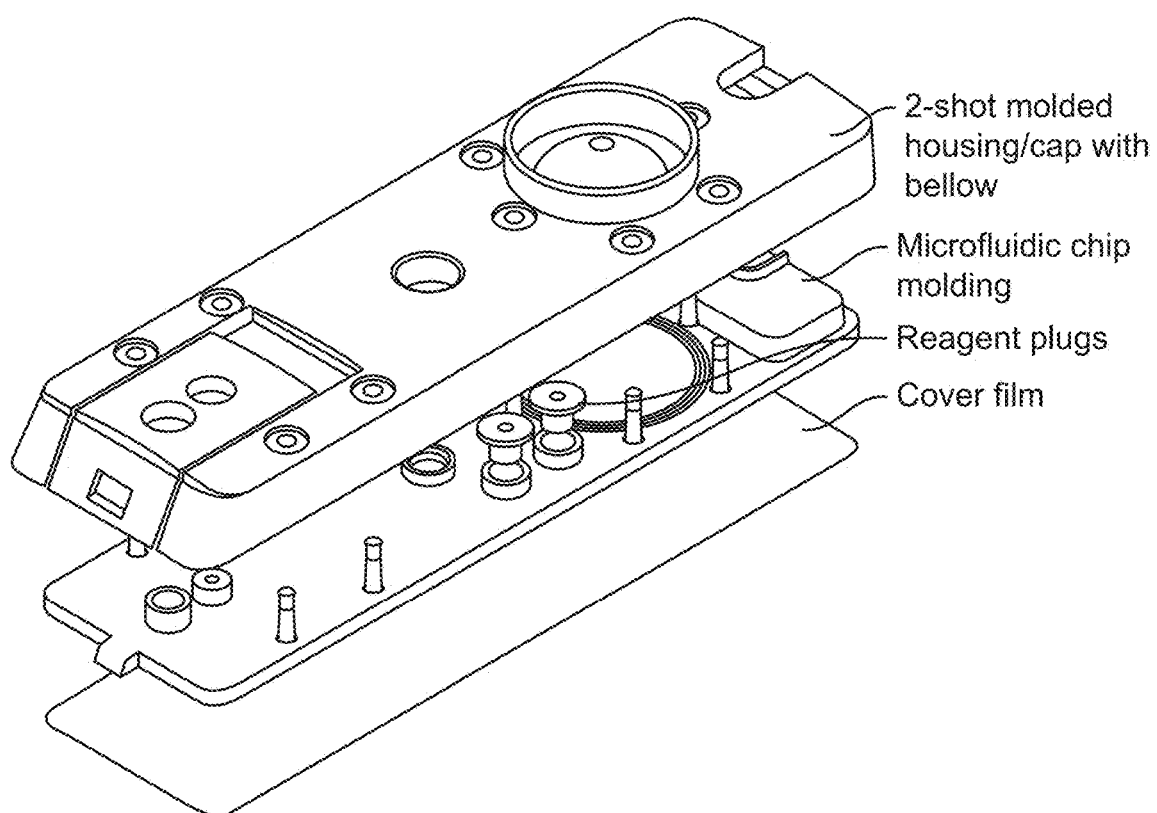
FIG. 19 shows a non-limiting example of a cartridge and housing according to the methods and embodiments disclosed herein.
Figure 20:
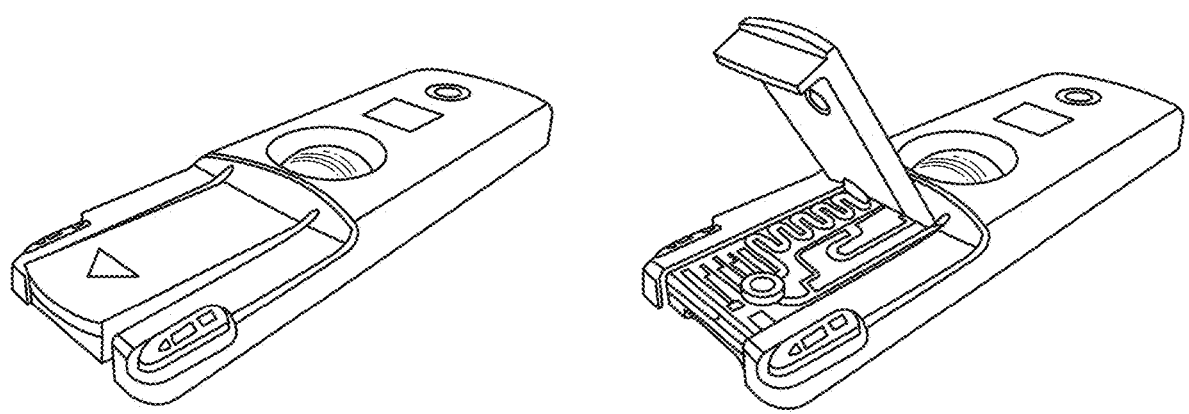
FIG. 20 shows a non-limiting example of a cartridge and housing according to the methods and embodiments disclosed herein.
Figure 21:
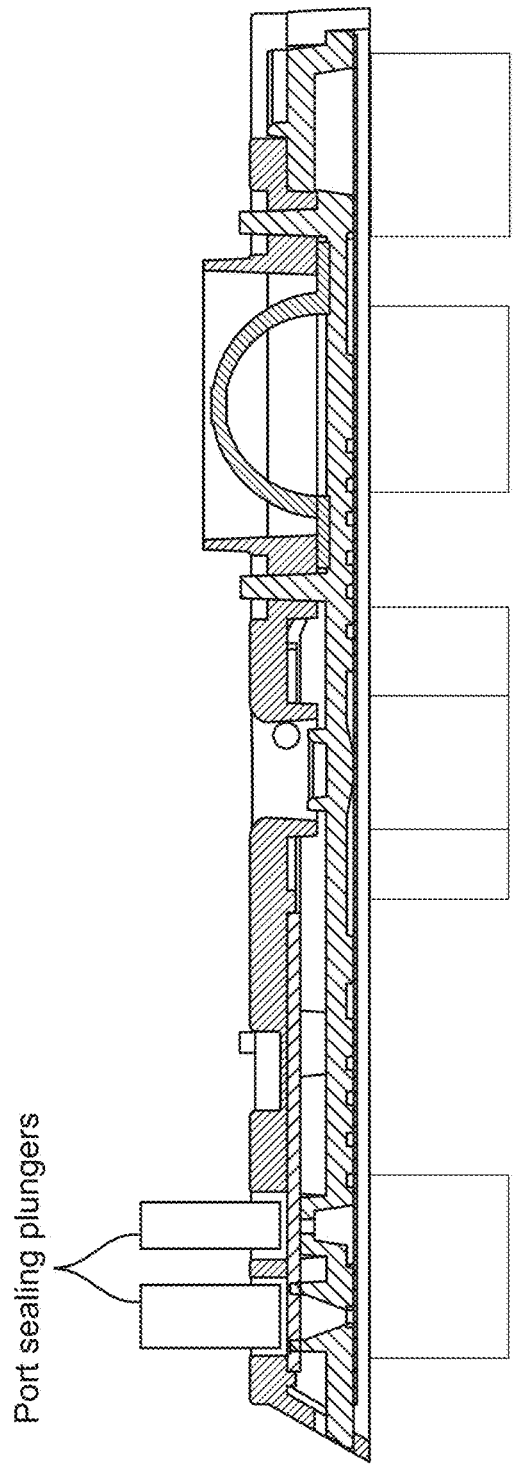
FIG. 21 shows a non-limiting example of a cartridge according to the methods and embodiments disclosed herein, with further details regarding port sealing plungers.
Figure 22:
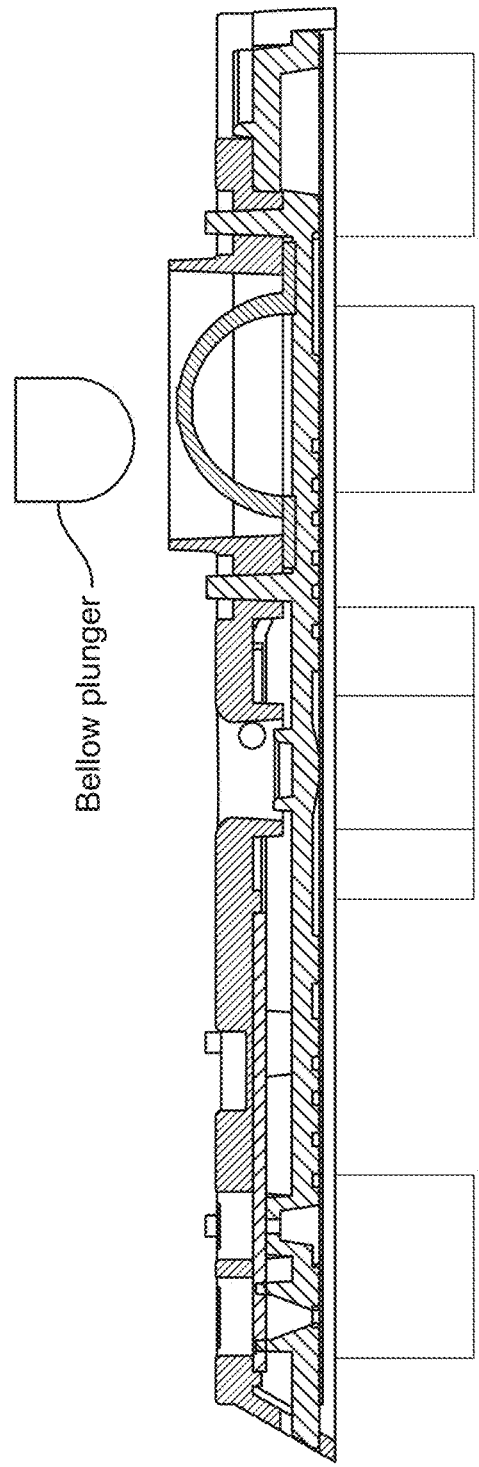
FIG. 22 shows a non-limiting example of a cartridge according to the methods and embodiments disclosed herein, with further details regarding with further details regarding the incorporation of a bellows plunger for fluidic movement through the cartridge.
Figure 23:
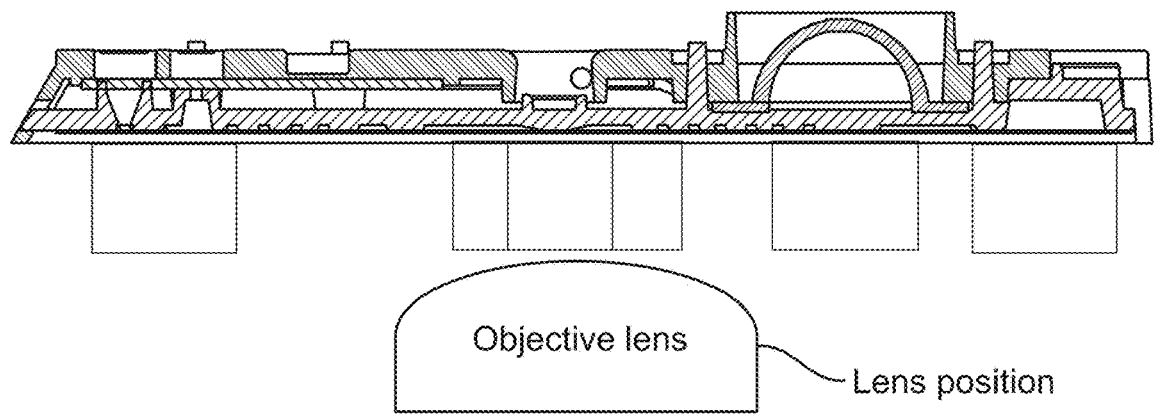
FIG. 23 shows a non-limiting example of a cartridge according to the methods and embodiments disclosed herein, with further details regarding the incorporation of objective lens of a detection module below or underneath the detection window of the cartridge.
Figure 24:
FIG. 24 shows non-limiting examples of the plug, which is incorporated into the cartridge. The plug operably maintains pressure within the cartridge to aid in fluidic movement. The plug may optionally incorporate reagents ("conical reagent surface") for mixing with the sample.

On-chip mixing structures are featured in an assay cartridge, wherein the fluidic channels include at least one, preferably a plurality of meandering mixing microchannels. See, e.g., FIG. 17 and FIG. 18. Although fluid flow in straight channels with the same dimensions are laminar, the meandering micro channel generate Deans flow where inertia of fluid can generate turbulence at the curved channel regions. The inertia induced turbulence enhances the mixing significantly to ensure sample is thoroughly mixed with reagents.

Example 7—Particle Counting to Analyze Cell Lysate

Figure 25:
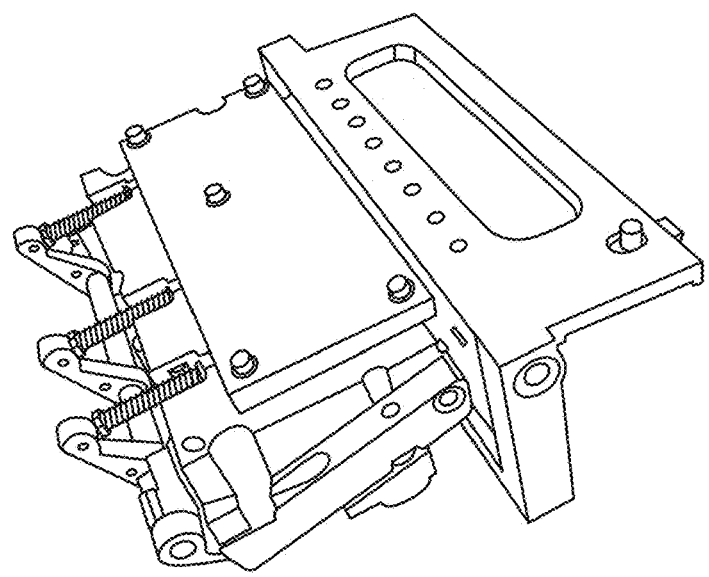
FIG. 25 shows a non-limiting example of the cartridge loading mechanism, including a cam assembly, plunger assembly, and door.
Figure 26:
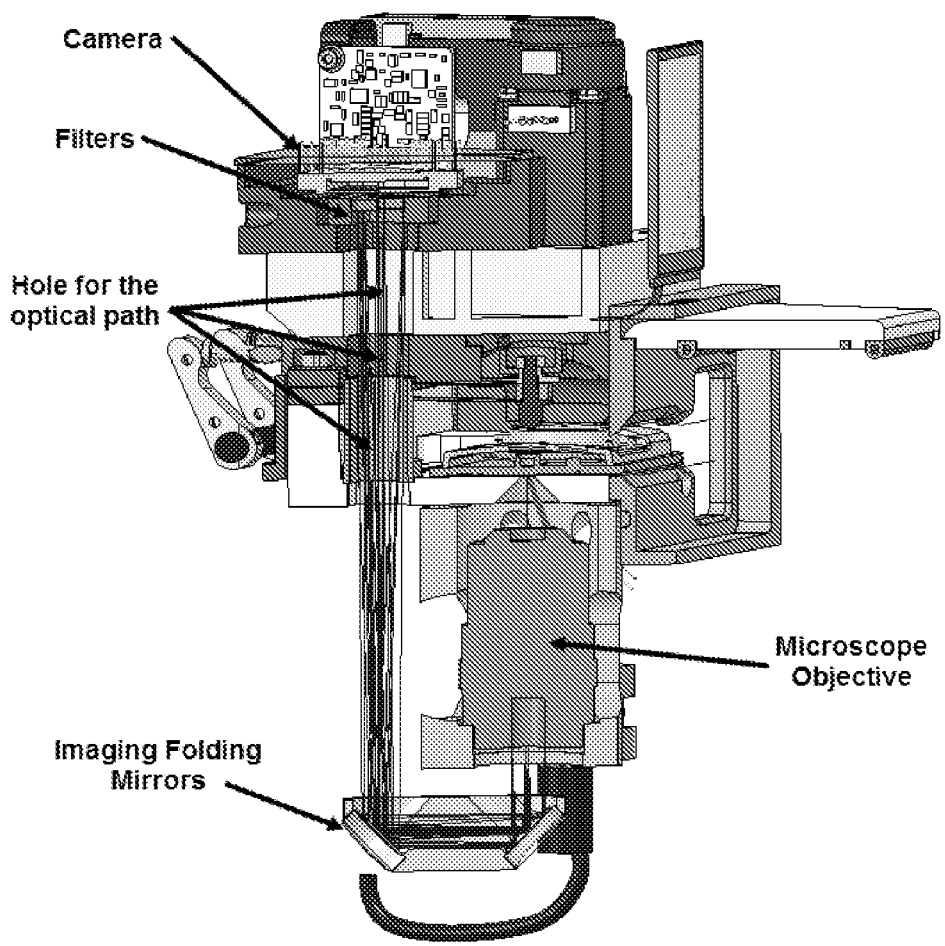
FIG. 26 shows a non-limiting example of the detection module, including optional configuration of the optical imaging system.

A user performs analysis of a cell sample, using the cartridges disclosed in FIGS. 19-24. A sample plug is disclosed in FIG. 25. The user lyses the cells in a sample using conventional laboratory techniques. The user then introduces the cell lysate to the microfluidic chip. The organelles within the cell lysate bind to antibody-labelled beads within the sample preparation chamber. The antibody-labelled beads flow through the microfluidic channel to the interrogation chamber, where the detection module takes and stores images of the beads for further analysis.

What is claimed is:

1. A cartridge for cell or particle detection and analysis comprising:
   a. one or more housing units;
   b. a fluidic chip incorporating at least one microfluidic channel comprising a plurality of meandering mixing microchannels that one or more cells or particles of a sample flows through within the fluidic chip, wherein the fluidic chip comprises at least a bellow actuator that drives either capillary or mechanical flow of the one or more cells or particles of the sample and together with the plurality of meandering mixing microchannels aid mixing of the sample with one or more reagents required for detection and analysis, wherein the one or more reagents are located downstream of at least one of the meandering mixing microchannels, and wherein the meandering mixing microchannels are non-symmetrical or non-uniform within the cartridge and generate turbulence within the microfluidic channel to enhance mixing of the reagents and sample;
   c. a detection window incorporated in one of the one or more housings, the detection window being operable to facilitate capture of one or more images of the one or more cells or particles of the sample flowing within the detection window.

2. The cartridge of claim 1, the fluidic chip further comprising:
   a. an inlet through which the sample is introduced to the microfluidic channel;
   b. an outlet through which the sample is removed from the fluidic chip; and
   c. a waste reservoir positioned near the outlet, the waste reservoir being operable to collect the sample after the sample has flowed through the microfluidic chip.

3. The cartridge of claim 1, wherein the detection window and a detection module are operable to apply multi-fluorescence detection.

4. The cartridge of claim 1, wherein sample preparation is integrated into the cartridge or wherein all reagents required for a test are supplied and sealed in the cartridge, and combinations thereof.

5. The cartridge of claim 4, wherein the reagents are dried or lyophilized or slow dried on the chip.

6. The cartridge of claim 4, wherein the reagents on the cartridge have a shelf life of at least 12 months at 0° C. to 40° C.

7. The cartridge of claim 4, wherein the reagents on the cartridge have a shelf life of at least 48 hours with temperature fluctuations between 0° C. and 50° C.

8. The cartridge of claim 1, wherein the cartridge holds a maximum volume of 200 microliters.

9. The cartridge of claim 1, wherein the cartridge requires a minimum of 2 microliters for analysis.

10. The cartridge of claim 1, wherein a sample size is 100 microliters or less.

11. The cartridge of claim 1, wherein the cartridge is marked with a unique identification number.

* * * * *